(12) United States Patent
Kim

(10) Patent No.: US 10,206,644 B2
(45) Date of Patent: Feb. 19, 2019

(54) X-RAY IMAGING APPARATUS

(71) Applicant: Samsung Electronics Co., Ltd., Gyeonggi-do (KR)

(72) Inventor: Eui Sik Kim, Seoul (KR)

(73) Assignee: Samsung Electronics Co., Ltd., Yeongtong-gu, Suwon-si, Gyeonggi-do (KR)

( * ) Notice: Subject to any disclaimer, the term of this patent is extended or adjusted under 35 U.S.C. 154(b) by 37 days.

(21) Appl. No.: 14/957,824

(22) Filed: Dec. 3, 2015

(65) Prior Publication Data
US 2016/0166222 A1      Jun. 16, 2016

(30) Foreign Application Priority Data

Dec. 12, 2014  (KR) .................. 10-2014-0179762

(51) Int. Cl.
| | |
|---|---|
| *A61B 6/00* | (2006.01) |
| *A61B 6/04* | (2006.01) |
| *A61B 6/08* | (2006.01) |
| *A61B 6/02* | (2006.01) |

(52) U.S. Cl.
CPC ............ *A61B 6/502* (2013.01); *A61B 6/0414* (2013.01); *A61B 6/0492* (2013.01); *A61B 6/46* (2013.01); *A61B 6/025* (2013.01); *A61B 6/08* (2013.01); *A61B 6/4233* (2013.01); *A61B 6/463* (2013.01); *A61B 6/54* (2013.01)

(58) Field of Classification Search
CPC ....... A61B 6/469; A61B 6/4441; A61B 6/587; A61B 5/748; A61B 6/547; A61B 6/4452; G03B 42/02

USPC ........ 378/11, 15, 39, 206, 166, 25, 98, 98.2, 378/98.3
See application file for complete search history.

(56) References Cited

U.S. PATENT DOCUMENTS

| 6,104,778 A | 8/2000 | Murad |
| 2010/0135562 A1 | 6/2010 | Greenberg et al. |

(Continued)

FOREIGN PATENT DOCUMENTS

| DE | 102008006115 A1 | 7/2009 |
| JP | 2011-250842 A | 12/2011 |

OTHER PUBLICATIONS

PCT International Search Report dated Mar. 31, 2016.
European Search Report dated Dec. 20, 2017.
European Search Report dated May 18, 2018.

*Primary Examiner* — Don Wong
(74) *Attorney, Agent, or Firm* — Cha & Reiter, LLC.

(57) ABSTRACT

An X-ray imaging apparatus according to the disclosure guides the patient posture using a visual and/or audible interaction device during execution of an X-ray imaging procedure such as mammography, and provides the patient with information about the procedure during the procedure's execution, thereby improving the patient experience while reducing the workload of an operator. The X-ray imaging apparatus may include an X-ray tube, an X-ray detector, and an arm including an upper end within which the X-ray tube is disposed, and a lower end within which the X-ray detector is disposed. An illumination unit may be configured to provide an indication of a movement direction of the arm, responsive to a user input for moving the arm in the movement direction. A controller may control the illumination unit.

13 Claims, 28 Drawing Sheets

(56) References Cited

U.S. PATENT DOCUMENTS

| | | | |
|---|---|---|---|
| 2011/0087132 A1* | 4/2011 | DeFreitas | A61B 90/17 600/567 |
| 2012/0053455 A1 | 3/2012 | Okada | |
| 2013/0136232 A1 | 5/2013 | Bouvier et al. | |
| 2013/0243160 A1* | 9/2013 | Graumann | A61B 6/54 378/91 |
| 2013/0345543 A1 | 12/2013 | Steibel, Jr. et al. | |
| 2014/0037058 A1* | 2/2014 | Allen | H05G 1/02 378/62 |
| 2014/0072105 A1* | 3/2014 | Belei | A61B 6/0457 378/62 |
| 2014/0112563 A1 | 4/2014 | Ruth et al. | |

* cited by examiner

X-RAY IMAGING APPARATUS

CLAIM OF PRIORITY

This application claims the benefit under 35 U.S.C. § 119 of Korean Patent Application No. 10-2014-0179762, filed on Dec. 12, 2014 in the Korean Intellectual Property Office, the entire disclosure of which is expressly incorporated herein by reference.

BACKGROUND

1. Field

Embodiments of the present disclosure relate generally to an X-ray imaging apparatus, and more particularly to an X-ray imaging apparatus configured to generate an X-ray image by transmitting X-rays to a breast of a human.

2. Description of the Related Art

X-ray imaging apparatuses are devices that irradiate an object (e.g. patient) with X-rays and acquire an image of the interior of the object using X-rays passing through the object. X-ray transmittance varies according to properties of materials constituting the object, and thus, an internal structure of the object may be imaged by detecting the intensity of X-rays having passed through the object.

An X-ray imaging technique to image the breast of a human body is referred to as mammography. Since mammary gland tissues and fat tissues grow in the breast in a different way than in other parts of the human body, X-ray imaging is performed in a state in which the breast disposed between an X-ray tube and an X-ray detector is compressed by a compression paddle so as to obtain an accurate and clear X-ray image of an inner structure of the breast.

In order to perform mammography, posture maintenance of a patient under the condition that the breast is compressed by the compression paddle is of importance to acquisition of a high-quality X-ray image of the breast. However, the maintenance of a requisite posture may cause patient pain and also increase the workload of a radiologist who guides the patient posture.

SUMMARY

An aspect of the present disclosure is to provide an X-ray imaging apparatus configured to guide the patient posture as well as to provide the patient with information about the procedure (e.g. a workflow) using a visual or audible interaction device during execution of the mammography, such that the patient can feel comfortable, workload of a radiologist can be reduced, and accuracy of X-ray imaging can be improved.

Additional aspects of the disclosure will be set forth in part in the description which follows and, in part, will be apparent from the description, or may be learned by practice of the technology disclosed herein.

In accordance with an aspect of the present disclosure, an X-ray imaging apparatus may include an X-ray tube, an X-ray detector, and an arm including an upper end within which the X-ray tube is disposed, and a lower end within which the X-ray detector is disposed. An illumination unit may be configured to provide an indication of a movement direction of the arm, responsive to a user input for moving the arm in the movement direction. A controller may control the illumination unit.

In accordance with another aspect of the present disclosure, an X-ray imaging apparatus includes: a tube head to which an X-ray tube is mounted; a detector mounting unit to which an X-ray detector is mounted; an arm including an upper end to which the tube head is mounted, and a lower end to which the detector mounting unit is mounted; a sub-display unit detachably mounted to at least one of the arm and a gantry supporting the arm; and a controller configured to control the sub-display unit.

BRIEF DESCRIPTION OF THE DRAWINGS

These and/or other aspects of the disclosure will become apparent and more readily appreciated from the following description of the embodiments, taken in conjunction with the accompanying drawings of which.

DETAILED DESCRIPTION

Figure 1:
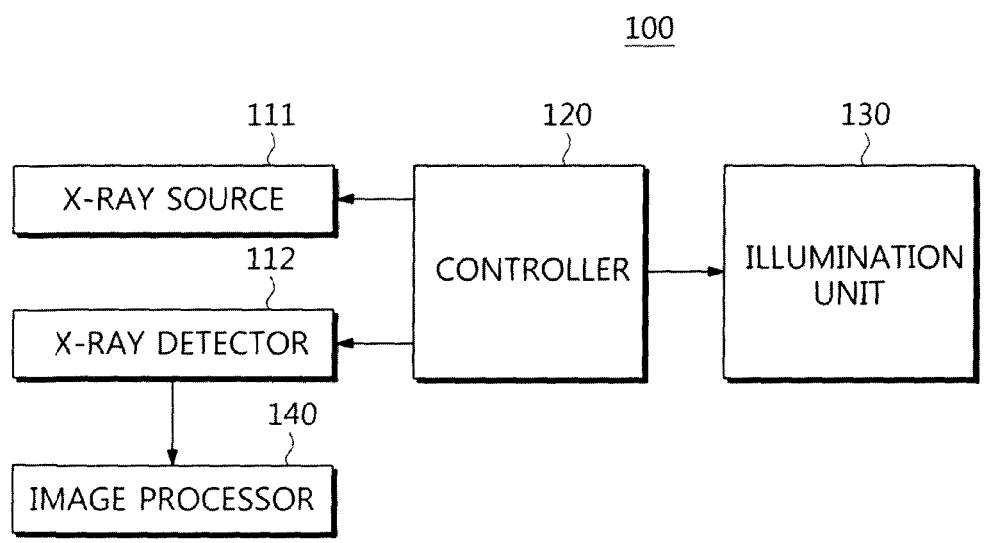
FIG. 1 is a functional block diagram illustrating an X-ray imaging apparatus according to an embodiment of the present disclosure.

Reference will now be made in detail to the embodiments of the present disclosure, examples of which are illustrated in the accompanying drawings, wherein like reference numerals refer to like elements throughout. The X-ray imaging apparatus according to various embodiments of the present disclosure will hereinafter be described with reference to the annexed drawings.

Herein, the term "user" may refer to either a patient whose breast is imaged by an X-ray apparatus, or an operator of the X-ray apparatus, e.g. a radiologist, a technician, a physician, etc. The term "object" may refer to an item of interest being X-rayed, such as a patient's breast.

Figure 2:
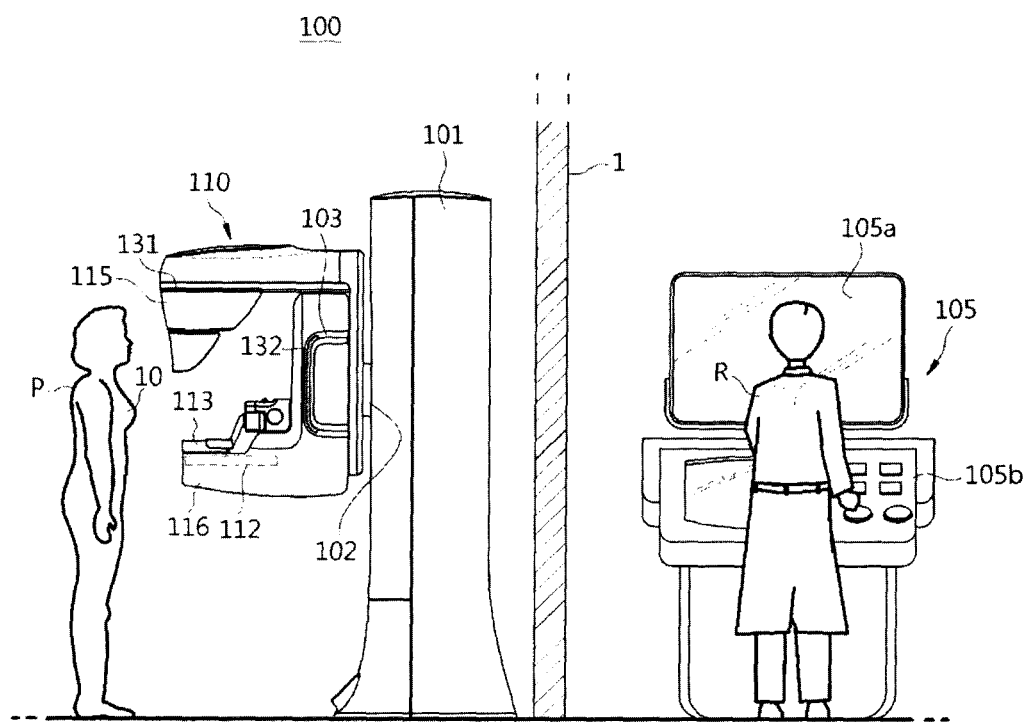
FIG. 2 illustrates the external appearance of an X-ray imaging apparatus according to an embodiment of the present disclosure.
Figure 3:
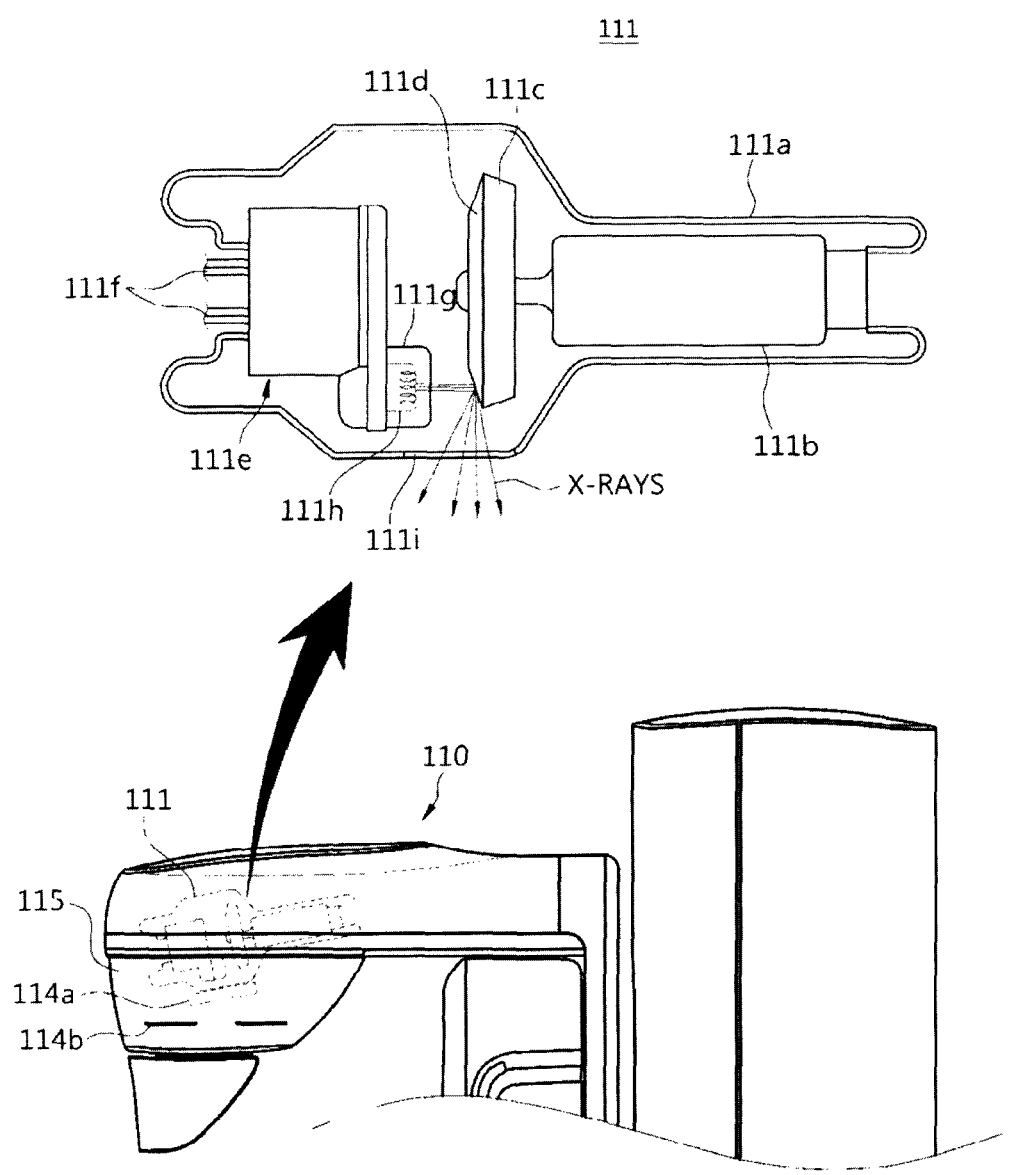
FIG. 3 is a structural view illustrating an X-ray tube.

FIG. 1 is a functional block diagram illustrating an X-ray imaging apparatus, 100, according to an embodiment of the present disclosure. FIG. 2 illustrates an example external appearance of an X-ray imaging apparatus 100, while FIG. 3 is an example structural view illustrating an X-ray tube.

Referring to FIG. 1, the X-ray imaging apparatus 100 includes an X-ray source 111 (hereafter referred to as an X-ray tube) for generating X-rays and emitting the X-rays to an object; an X-ray detector 112 for detecting X-rays having passed through the object, and converting the X-rays into an electrical signal; an illumination unit 130 for guiding users (e.g. patient or radiologist), providing the users with feedback information, or providing the users with procedural information; a controller 120 for controlling overall operations of the X-ray tube 11, the X-ray detector 112, and the illumination unit 130; and an image processor 140 for generating an X-ray image derived from the electrical signal.

The X-ray tube 111 may generate X-rays according to scan parameters suitable for the object characteristics or the scanning purpose, and may emit the X-rays to the object. The scan parameter may be established by a user, or may be automatically established by the controller 120.

The X-ray detector 112 may detect X-rays emitted from the X-ray tube 111 and passed through the object, and may generate an electrical signal corresponding to the detected X-rays. The generated electrical signal may be transmitted to the image processor 140. The electrical signal applied to the image processor 140 may be a digital signal or an analog signal. In the case of a digital signal, an analog-to-digital converter (ADC) is contained in the X-ray detector 112 such that the analog electrical signal is converted into the digital signal and the digital signal is then provided to the image processor 140.

The controller 120 may control the operations of the illumination unit 130. For example, on and off states of lighting, blinking, coloring, dimming, etc. of the illumination unit 130 can be controlled by the controller 120. In addition, the controller 120 may control the operations of the X-ray tube 111 or the X-ray detector 112. For example, the controller 120 may perform the auto exposure control operation for automatically establishing the scan parameter, or may control the operation for reading out the electrical signal using the X-ray detector 112. The illumination unit may include elements such as a headlamp 131 and a handle lamp 132, discussed below, which may provide the user with visual interaction information.

The controller 120 may include a memory configured to store a program associated with the above-mentioned control operation; and a processor configured to execute the program stored in the memory. The controller 120 may include a single memory and a single processor, or may include plural memories or plural processors. If the controller 120 includes plural memories or plural processors, the memories and processors may be integrated into one chip, may be physically contained in the same module, or may also be physically contained in different modules as necessary. For example, some parts of the plural processors may be contained in a workstation 105 of the X-ray imaging apparatus 100, while other parts of the plural processors may be contained in the arm 110 or the gantry 101. In other words, there is no limitation in physical positions of the processors or memories constructing the controller 120.

The image processor 140 may generate an X-ray image of the object using electrical signals received from the X-ray detector 112. To improve readability of an X-ray image thus generated, e.g., to a degree needed for checking the internal structure or lesions of the object, the image processor 140 may perform various signal processing algorithms to enhance an image for display on the display unit 151.

Image processing performed by the image processor 140 may include a pre-processing step and a post-processing step. The pre-processing step may include gain correction, offset correction, flat field correction, etc. The post-processing step may include noise correction, contrast correction, sharpness correction, brightness correction, etc. for image improvement or image enhancement.

The image processor 140 may include a memory storing a program associated with the above-mentioned processing operation; and a processor capable of executing the program stored in the memory. In addition, the image processor 140 may include a single memory and a single processor, or may include plural memories or plural processors. The image processor 140 may share all or some parts of the memories or processors of the controller 120.

The X-ray imaging apparatus 100 according to an embodiment of the present disclosure can capture an X-ray image of the breast from among physical parts of the patient. The X-ray imaging apparatus 100 will hereinafter be described with reference to the example physical structure of FIG. 2.

Referring to FIG. 2, an example X-ray imaging apparatus 100 for capturing an image of the breast of a human body has a specific structure in which an arm 110 is connected to a gantry 101 through a connection unit 102. The gantry 101 may support the arm 110. The X-ray tube 111 is embedded in an upper part of the arm 110, while the X-ray detector 112 is embedded in a lower part of the arm 110. The upper part of the arm 110 housing the X-ray tube 111 will hereinafter be referred to as a tube head 115, and the lower part of the arm 110 housing the X-ray detector 112 will hereinafter be referred to as a detector mounting unit 116. The detector mounting unit 116 may also be referred to as a bucky.

If the breast 10 of the patient P is placed between the X-ray tube 111 and the X-ray detector 112 (e.g. held in place via a compression paddle 113 as in a convention mammography apparatus), the X-ray tube 111 emits X-rays to the breast, and the X-ray detector 112 detects the X-rays having passed through the breast and converts the X-rays into an electrical signal. The electrical signal is routed to the image processor 140 such that an X-ray image of the breast can be formed.

Referring to FIG. 3, the X-ray tube 111 may be implemented as a bipolar vacuum tube including an anode 111c and a cathode 111e. The tube may be a glass tube 111a formed of hard silicic acid and the like.

The cathode 111e may include a filament 111h and a focusing electrode 111g. The focusing electrode 111g may also be referred to as a focusing cup. The inner space of the glass tube 111a is evacuated to a high-vacuum state of about 10 mmHg, and the filament 111h of the cathode 111e is heated to high temperature to generate thermoelectrons. The filament 111h may be, for example, a tungsten filament and may be heated by applying a current to an electrically conductive wire 111f connected to the filament 111h.

The anode 111c may be formed of, for example, copper (Cu). A target material 111d is deposited or arranged at a side facing the cathode 111e. For example, the target material may be formed of a high-resistance material, for example, chromium (Cr), iron (Fe), cobalt (Co), nickel (Ni), tungsten (W), molybdenum (Mo), rhodium (Rh), or the like. The types of target materials may be determined according to characteristics of the object. For example, if an image of the breast having dense tissues is captured, high-energy X-rays may be generated using tungsten (W) or rhodium (Rh), and low-energy X-rays may be generated using molybdenum (Mo).

If a high voltage is applied between the cathode 111e and the anode 111c, thermoelectrons are accelerated and collide with the target material 111d of the anode 111c, thereby generating X-rays. The generated X-rays are radiated outside through a window 111i that may be formed as a thin beryllium (Be) film.

In this case, a filter 114a may be located on a front surface of the window 111i to filter X-rays having a certain energy band. The filter 114a may be formed of, for example, molybdenum (Mo), rhodium (Rh), yttrium (Y), aluminum (Al), etc. Since energy bands suctioned into respective materials differ from each other, the filter 114 may be formed of an optimum material suitable for each energy band of X-rays to be irradiated. For example, the filter 114a may be formed of molybdenum (Mo) so as to absorb low-energy X-rays. The filter 114a may be formed of aluminum (Al) so as to absorb X-rays having energy of 30 kVp or higher.

The anode 111c may be rotated by a rotor 111b. If the anode 111c rotates, compared to a case in which the anode 111c is fixed, a heat accumulation rate per unit area may be increased by 10 times or more, and the size of the focal point is reduced.

A voltage applied between the cathode 111e and the anode 111c is referred to as a tube voltage, and the magnitude thereof may be represented as peak kilovolts (kVp). If the tube voltage is increased, the speed of thermoelectrons is increased and thus the energy of X-rays (the energy of photons) generated due to collision of the thermoelectrons with the target material 111d is increased.

A current flowing in the X-ray tube 111 is referred to as a tube current and may be represented as average current (mA). If the tube current is increased, the dose of X-rays (the number of X-ray photons) is increased.

Accordingly, the energy of X-rays may be controlled by the tube voltage and the dose of X-rays may be controlled by the tube current and an X-ray exposure time. As a result, the energy and intensity of irradiated X-rays can be controlled according to categories or characteristics of the object.

If the irradiated X-rays have a predetermined energy band, the energy band may be defined by the upper limit and the lower limit. The upper limit of the energy band, i.e., maximum energy of the irradiated X-rays, may be adjusted by the magnitude of the tube voltage. The lower limit of the energy band, i.e., minimum energy of the irradiated X-rays, may be adjusted by the filter. If X-rays having a low-energy band are filtered by the filter, average energy of the irradiated X-rays may be increased.

A collimator 114b may be arranged at a front surface of the window 111i, such that the irradiation range of X-rays emitted through the window 111i may be adjusted, and X-ray scattering may be reduced.

The above-mentioned parameters, for example, a tube voltage, a tube current, an X-ray exposure time, a target material type, a filter type, a rotation speed of the anode, etc. may be used as scan parameters established by the user or the controller 120.

Figure 4:
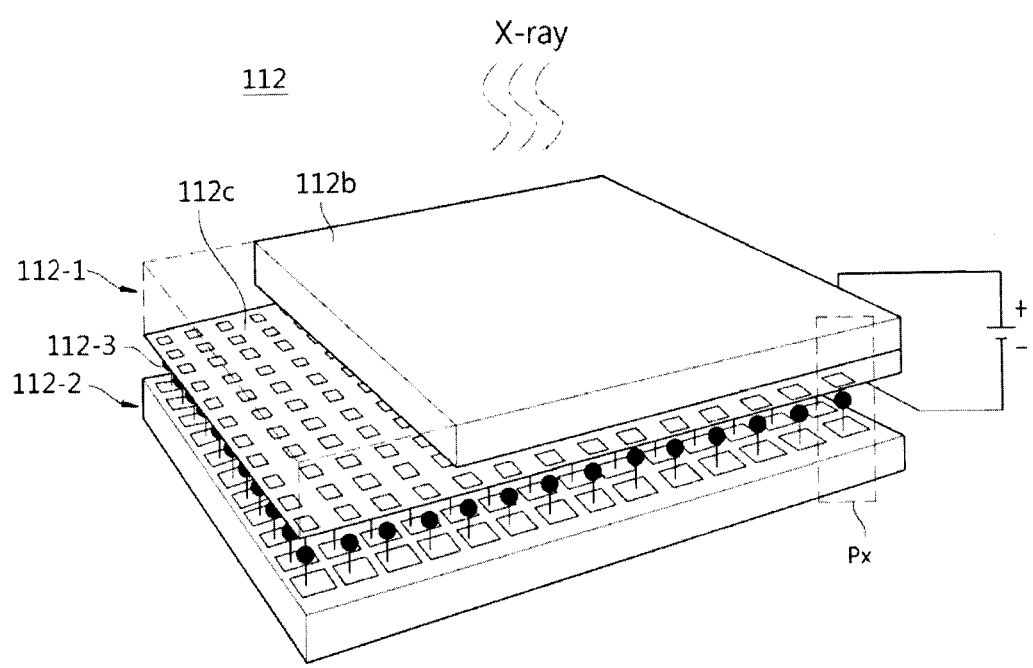
FIG. 4 is a structural view illustrating an X-ray detector.

FIG. 4 is a structural view illustrating an X-ray detector 112. X-ray detector 112 may include a light receiving element 112-1 for generating an electrical signal by detecting X-rays; and a readout circuit 112-2 for reading the generated electrical signal.

A monocrystalline semiconductor material may be used as the light receiving element 112-1 in order to secure high resolution, rapid response time and high dynamic range at low energy and low dose. Examples of the monocrystalline semiconductor material may include Ge, CdTe, CdZnTe, GaAs or the like.

The light receiving element 112-1 may be configured as a PIN photodiode in which a P-type semiconductor substrate 112c having a two-dimensional (2D) array structure is bonded to a bottom surface of a high-resistance N-type semiconductor substrate 112b.

The readout circuit 112-2 formed using a CMOS (Complementary Metal Oxide Semiconductor) process may form a 2D array structure, and may be combined with the P-type substrate 112c of the light receiving element 112-1 pixel by pixel. The CMOS readout circuit 112-2 and the light receiving element 112-1 may be combined through a flip chip bonding process. In this case, a bump 112-3 formed of solder (PbSn), indium (In) or the like is first formed, and the CMOS readout circuit 112-2 and the light receiving element 112-1 are pressed against each other while performing reflow soldering and applying heat.

The above-mentioned X-ray tube and X-ray detector structures are merely examples which may be employed within the X-ray imaging apparatus 100; other designs for these elements are available. It should be noted that the X-ray imaging apparatus 100 may include not only the above-mentioned structures but also other structures as necessary or desired.

Tissue of the breast 10 includes fibrous tissue surrounding the breast 10 and maintaining a shape thereof, fatty tissue present throughout the breast 10, a mammary gland tissue to produce milk and lactiferous duct tissue providing a passage of the milk. A tissue associated with production and supply of milk, such as the mammary gland tissue or the lactiferous duct tissue among these tissues, is referred to as fibroglandular tissue. As described above, since the breast consists entirely of soft tissues, there is a small difference in attenuation coefficient between constituent components of the breast. If the breast is compressed such that a thickness of the breast is reduced, a high-contrast image can be obtained with low dosage, and materials overlapping with each other in the vertical direction can be spread out.

Returning to FIG. 2, the X-ray imaging apparatus 100 may further include the compression paddle 113 disposed between the X-ray tube 111 and the X-ray detector 112. If the breast 10 is placed on the detector mounting unit 116, the compression paddle 113 may compress the breast 10, and the X-ray tube 111 may emit X-rays to the compressed breast 10. X-rays having passed through the breast 10 may be detected by the X-ray detector 112.

The workstation 105 may include a display unit 105a configured to display either an X-ray image obtained by scanning or a screen image associated with control of the X-ray imaging apparatus 100; and an input unit 105b configured to receive a control command regarding the X-ray imaging apparatus 100 from a user. A radiologist R may control scanning by manipulating the workstation 105, and thus confirm the acquired X-ray image. The terms "scanning" and "capturing" used herein may indicate the operation for imaging the internal part of the object by emitting X-rays to the object. As such, "scanning" and "capturing" may be used interchangeably herein.

In order to prevent unnecessary X-rays from being exposed to the radiologist R, a protective screen 1 for blocking X-rays may be installed between the workstation 105 and the gantry 101. The radiologist R located outside the protective screen 1 may control the position of the arm 110, and may establish the posture of the patient P. The radiologist R located inside the protective screen 1 may control scanning by manipulating the workstation 105. Alternatively, the workstation 105 and the gantry 101 may be located in different rooms. In conventional systems, such back and forth tasks of the radiologist R may undesirably increase his or her workload, which may deteriorate efficiency and result in low-quality images.

In addition, the patient P removes his or her jacket for the X-ray imaging of the breast 10, and must maintain a predetermined posture according to categories of mammograms. A patient who is nervous may have minimal understanding regarding the capturing progression situation. The patient may also have low adaptability regarding the instruction of the radiologist. As a result, with conventional apparatuses, the patient P may feel uncomfortable while the radiologist R may experience mental and physical distress, resulting in formation of a low-quality image.

As mentioned, the X-ray imaging apparatus 100 according to the present embodiment may include the illumination unit 130 for providing the user with visual interaction. The illumination unit 130 may provide the patient with procedural and/or posture information, and may also provide the radiologist with feedback information regarding the movement of the arm 110. In this embodiment, the procedural information may be comprised of a plurality of steps needed or desirable for X-ray imaging. One procedure may include a plurality of steps needed from the start time at which the patient enters a room (examination room) having the X-ray imaging apparatus 100 to the end time at which X-ray imaging of the patient is completed and the patient exits the room. In one set of steps of a given procedure(s), at least one type of X-ray imaging can be carried out.

The illumination unit 130 may include a headlamp 131 mounted to a tube head 115 of the arm 110; and a handle lamp 132 mounted to a handle or knob 103 of the arm 110. The headlamp 131 and the handle lamp 132 may provide the user with visual interaction information through at least one of coloring, turning lights on or off, and blinking thereof. The visual interaction may include an information provision process and a feedback process.

Coloring or blinking of the headlamp 131 or the handle lamp 132 is shown in different ways according to respective steps comprising the procedure, such that information regarding a current step can be supplied to the user. Moreover, an overall procedure may further include steps to be taken in an emergency situation. For example, if the emergency situation such as a malfunction of the device is detected, the headlamp 131 or the handle lamp 132 may be illuminated in red, and a blinking period may be set to a short time (causing rapid blinking).

In addition, the posture of the patient P may be guided through the headlamp 131 or the handle lamp 132, or the position arrangement of the arm 110 of the radiologist R may be guided.

Detailed embodiments for allowing the headlamp 131 and the handle lamp 132 to provide the user with the visual interaction information will hereinafter be described in detail.

Figure 5:
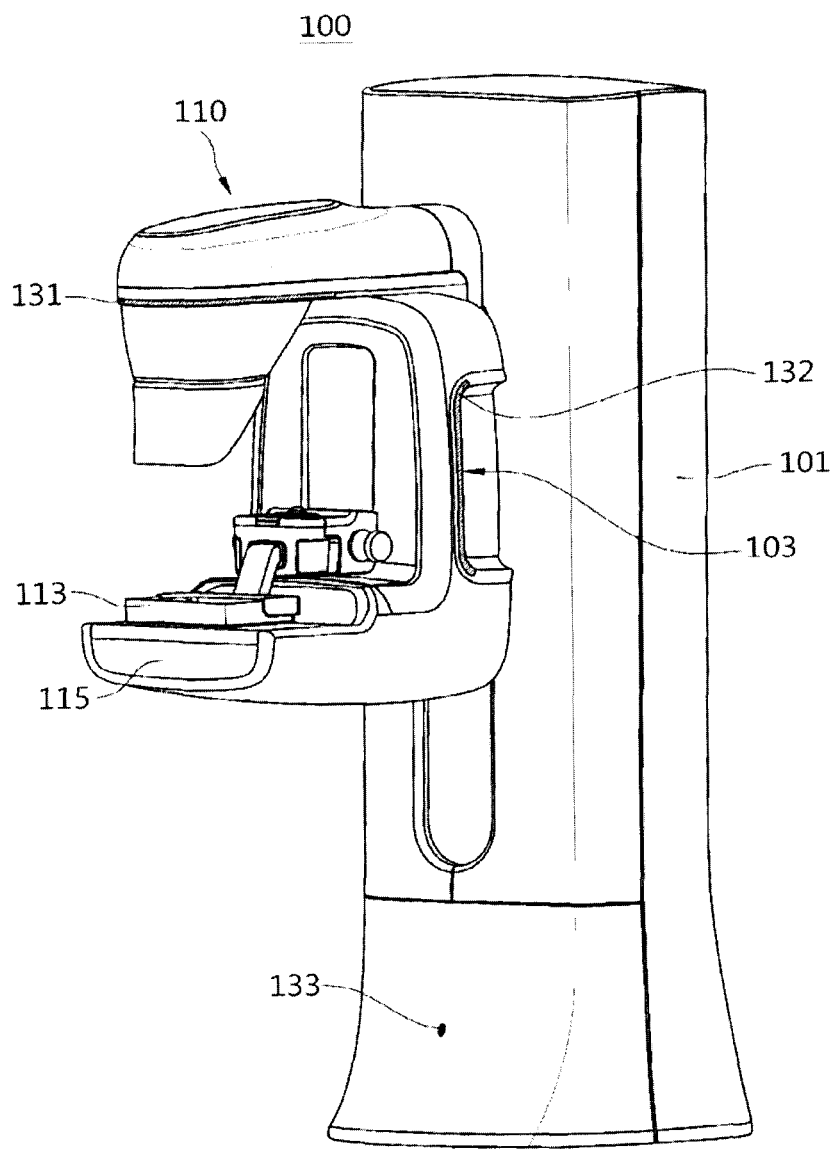
FIG. 5 illustrates the external appearance of an X-ray imaging apparatus further including a gantry lighting mounted to a gantry.
Figure 15:
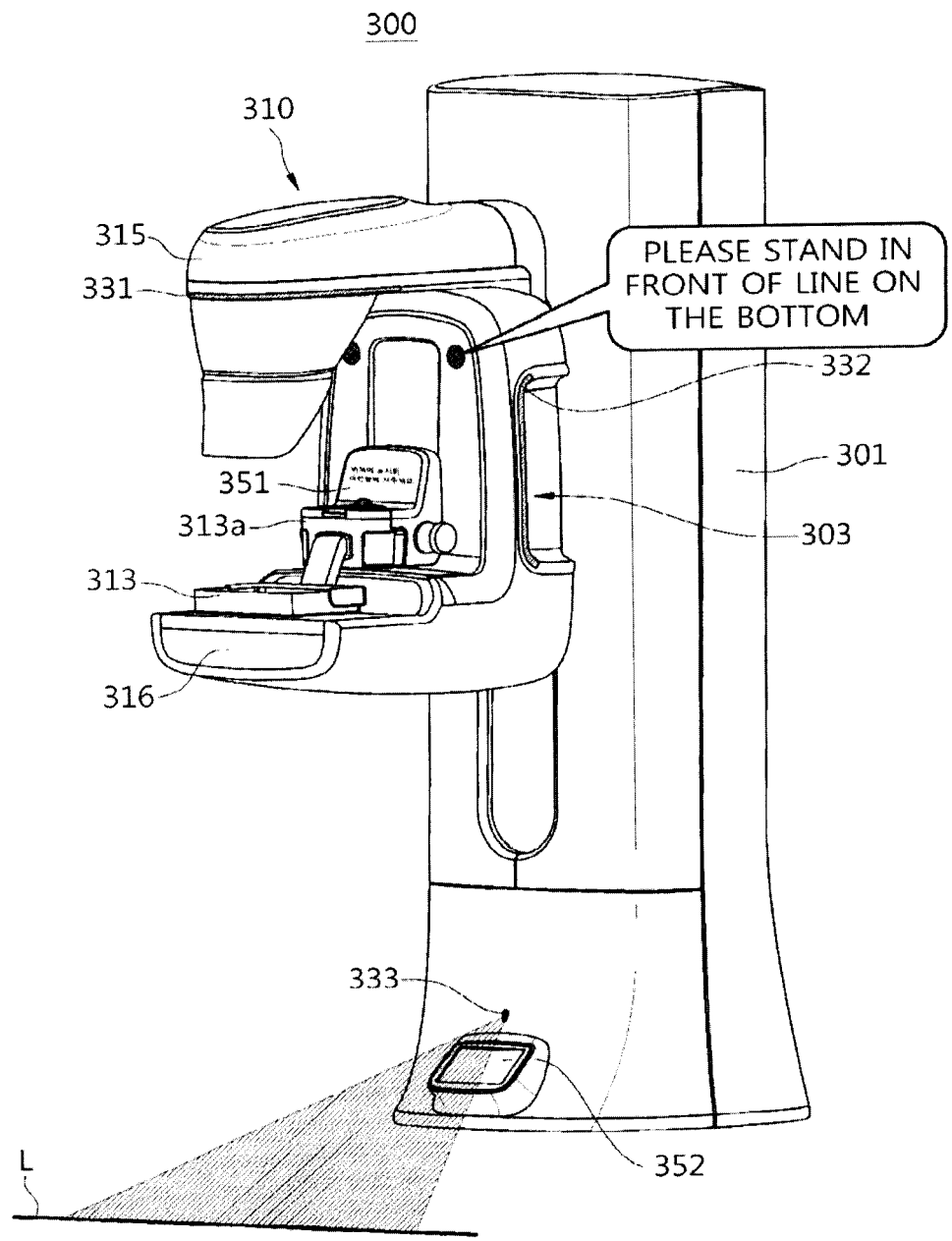
FIG. 15 illustrates audiovisual information provided when a patient enters an examination room.

FIG. 5 illustrates an example external appearance of an X-ray imaging apparatus further including a gantry lighting mounted to a gantry. The lamp unit 130 may further include a gantry lamp 133 mounted to the gantry 101. The gantry lamp 133 may be mounted to the bottom of the gantry 101 such that it can emit light to the ground, where the light emitted from the gantry lamp 133 may form a line (L) on the ground (as shown in FIG. 15).

A tilt angle of the gantry lamp 133 tilted toward the ground may be adjusted such that the position of the line (L) may also be adjusted. Therefore, the gantry lamp 133 forms the line (L) at an appropriate position to guide the position of the patient P to be X-ray imaged.

The headlamp 131, the handle lamp 132 or the gantry lamp 133 contained in the lamp unit 130 may be implemented as various types of light sources, for example, a semiconductor laser, a He—Ne laser, a halogen lamp, an LED lamp, etc.

Figure 6:
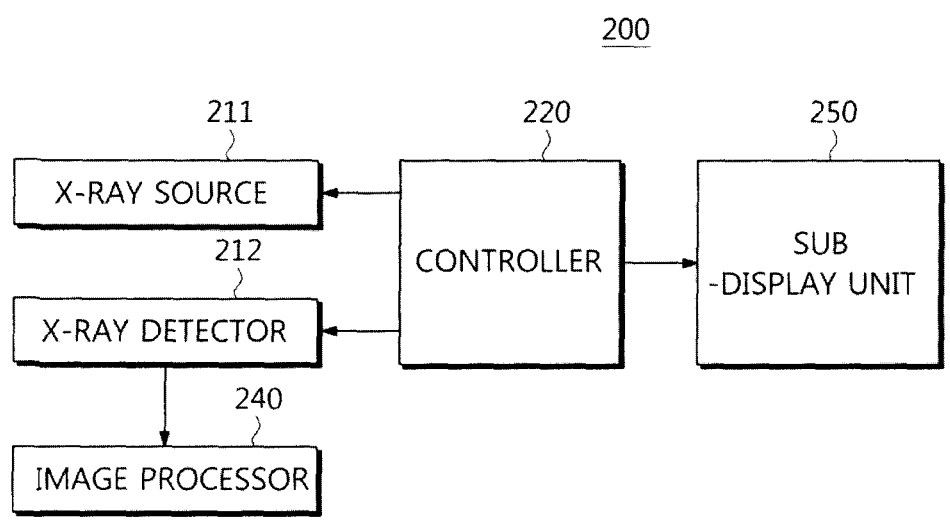
FIG. 6 is a functional block diagram illustrating an X-ray imaging apparatus according to another embodiment of the present disclosure.
Figure 7:
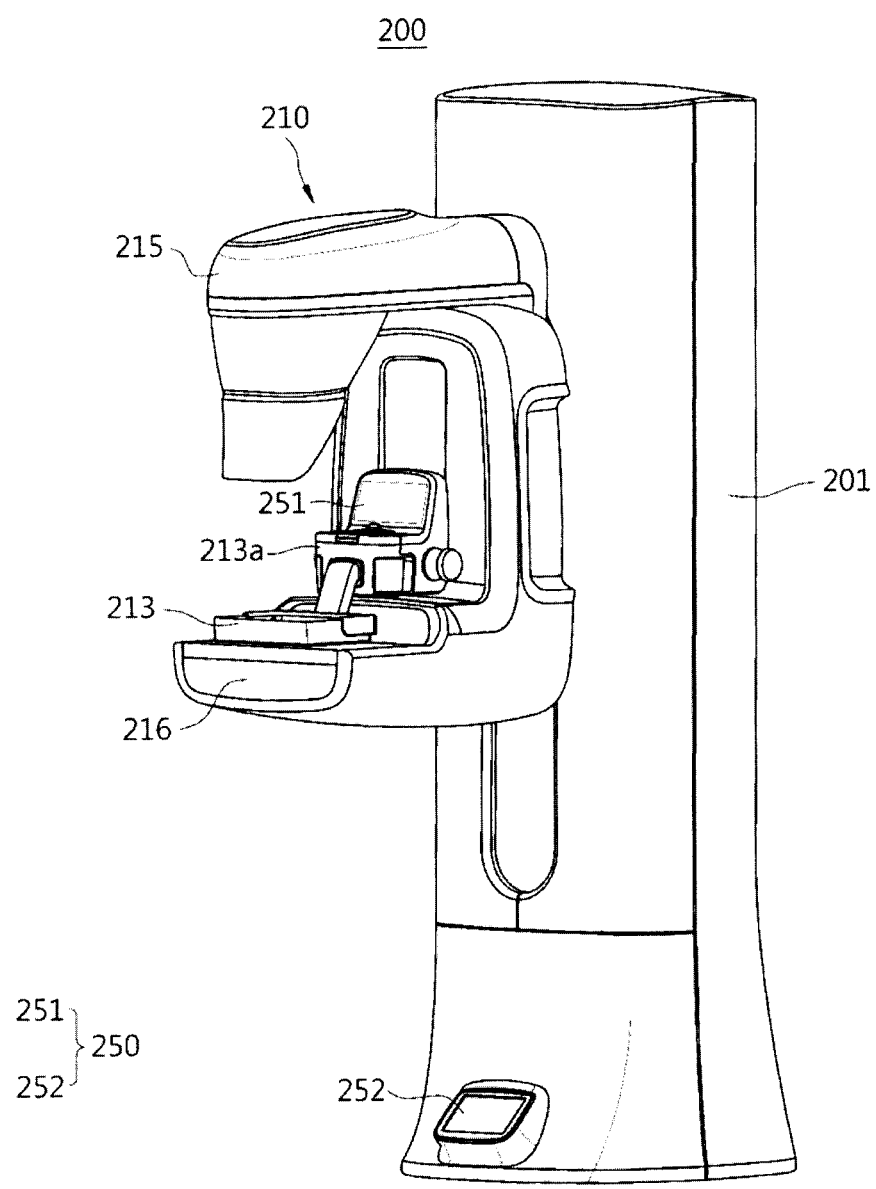
FIG. 7 illustrates an example external appearance of the X-ray imaging apparatus shown in FIG. 6.
Figure 8:
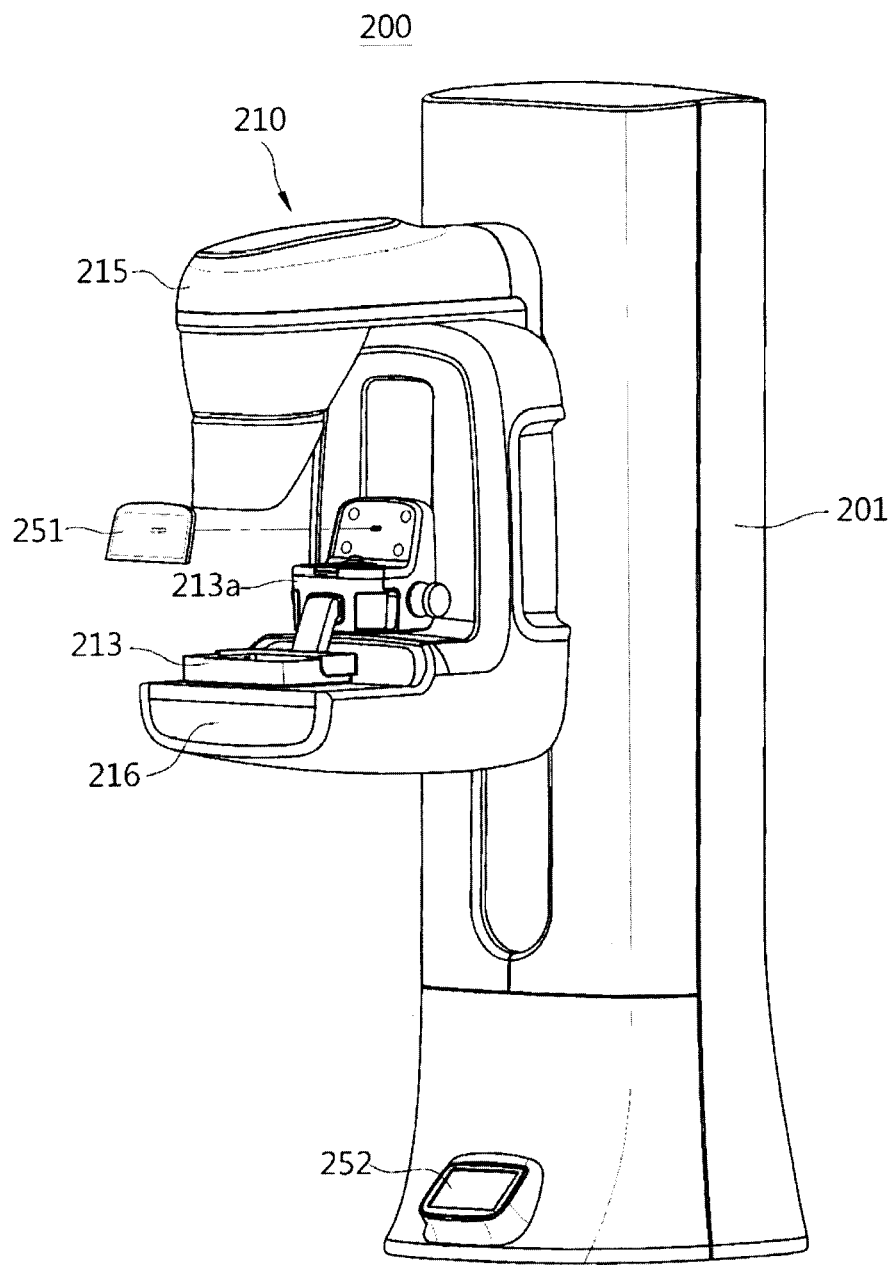
FIG. 8 illustrates an example external appearance of the X-ray imaging apparatus shown in FIG. 6.

FIG. 6 is a functional block diagram illustrating an X-ray imaging apparatus, 200, according to another embodiment of the present disclosure. FIGS. 7 and 8 illustrate example external appearances of the X-ray imaging apparatus shown in FIG. 6.

X-ray imaging apparatus 200 may include an X-ray tube 211, an X-ray detector 212, an image processor 240, and a sub-display unit 250.

The X-ray tube 211, the X-ray detector 212, and the image processor 240 may be identical to those of the X-ray tube 111, the X-ray detector 112, and the image processor 140 of the X-ray imaging apparatus 100, and as such a detailed description thereof will herein be omitted for convenience of description.

Although not shown in FIGS. 7 and 8, the X-ray imaging apparatus 200 may include a workstation that includes both a display unit configured to display either the captured X-ray image or a screen image associated with control of the X-ray imaging apparatus 200, and an input unit configured to receive a control command regarding the X-ray imaging apparatus 200 from the user.

The sub-display unit 250 may be arranged separately from the display unit mounted to the workstation. For example, as shown in FIG. 7, the sub-display unit 250 may include an arm display unit 251 mounted to the arm 210; and a gantry display unit 252 mounted to the gantry 201.

The arm display unit 251 may display procedural information of the X-ray imaging, information regarding the patient posture, information regarding the patient, information regarding the arm 210, and/or a captured X-ray image. The same and/or different content as displayed on arm display unit 251 may be displayed on the gantry display unit 252. By way of example, the patient may view the arm display unit 251 while the radiologist views the gantry display unit 252.

The gantry display unit 252 may display information regarding the arm 210 (specifically, information regarding pressure of the compression paddle 213), in order to direct the radiologist to establish the posture of the patient P.

The arm display unit 251 and the gantry display unit 252 may be implemented as at least one of various display devices, for example, a Liquid Crystal Display (LCD), a Light Emitting Diode (LED), a Plasma Display Panel (PDP), an Organic Light Emitting Diode (OLED), etc.

The controller 220 may control the overall operation of the X-ray imaging apparatus 200, and may control a screen image displayed on the sub-display unit 250. Controller 220 may be configured similarly to controller 120 described above.

Meanwhile, the arm display unit 251 may be detachably mounted to the arm 210, such that the arm display unit 251 can be freely mounted to or detached from the arm 210, as shown in FIG. 8. For instance, the arm display unit 251 may receive real time X-ray image data via a cable, or wirelessly, from a transmitter of the X-ray apparatus 200. Thus if the patient P is required to move from a current position to another position (e.g. sideways) after a first set of X-ray images of the patient has been captured, the patient may view subsequently taken X-ray images in the new position by holding the detached display unit 251. If the patient P raises the arm display unit 251 separated from the arm 210 and at the same time moves to another position, information regarding the X-ray image captured at the moved position can be immediately confirmed.

In addition, the arm display unit 251 may also be implemented as a mobile display device, for example, a smartphone, a tablet PC, a PDA, etc. In this case, the user may install an application capable of performing the above-mentioned operation into a mobile display device, such that the resultant mobile display device can be used as the arm display unit 251. During the X-ray imaging procedure, the user may mount the mobile display device to the arm 210 (whereby the arm 210 with device so mounted provides an alternative arm display unit 251). When the X-ray imaging is completed, the user may detach the mobile display device from the arm 210.

The detachable arm display unit 251 may be mounted to the arm 210 in various ways. For example, as shown in FIG. 8, the upper end of the pad mounting unit 213a is extended to form the surface capable of supporting the arm display unit 251. In addition, a groove may be formed in one region of the surface, and a protrusion may be formed at a back surface of the arm display unit 251, such that the arm display unit 251 can be mounted to or detached from the arm 210 via insertion and removal of the protrusion to and from the groove.

In another example, a magnet is attached to the back surface of the arm display unit 251, and another magnet is embedded in one region of the arm 210, such that the arm display unit 251 may also be mounted to the corresponding region via magnetic force.

In another example, the arm display unit 251 is mounted in a manner that the angle thereof can be adjusted, such that the angle of the arm display unit 251 can also be adjusted according to user convenience.

Figure 9:
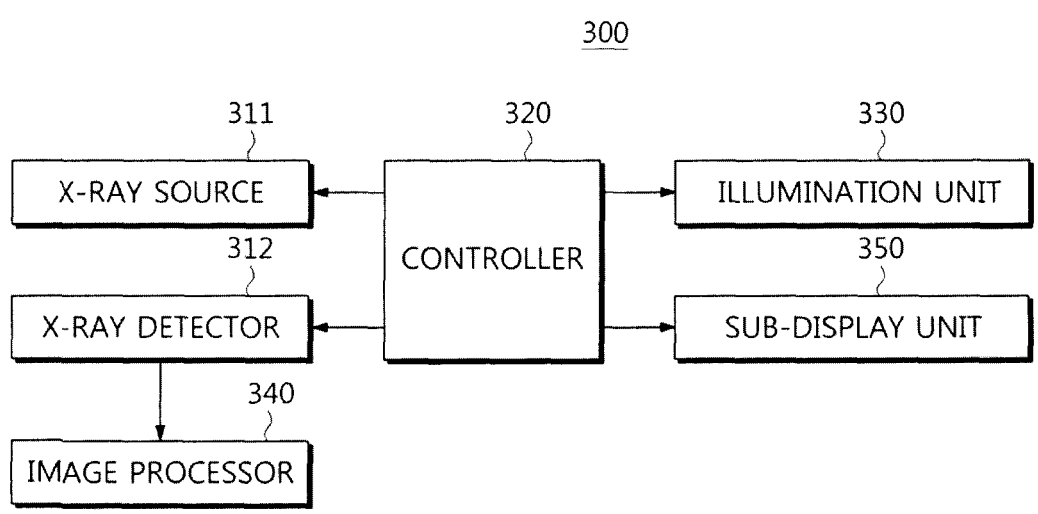
FIG. 9 is a functional block diagram illustrating an X-ray imaging apparatus according to another embodiment of the present disclosure.
Figure 10:
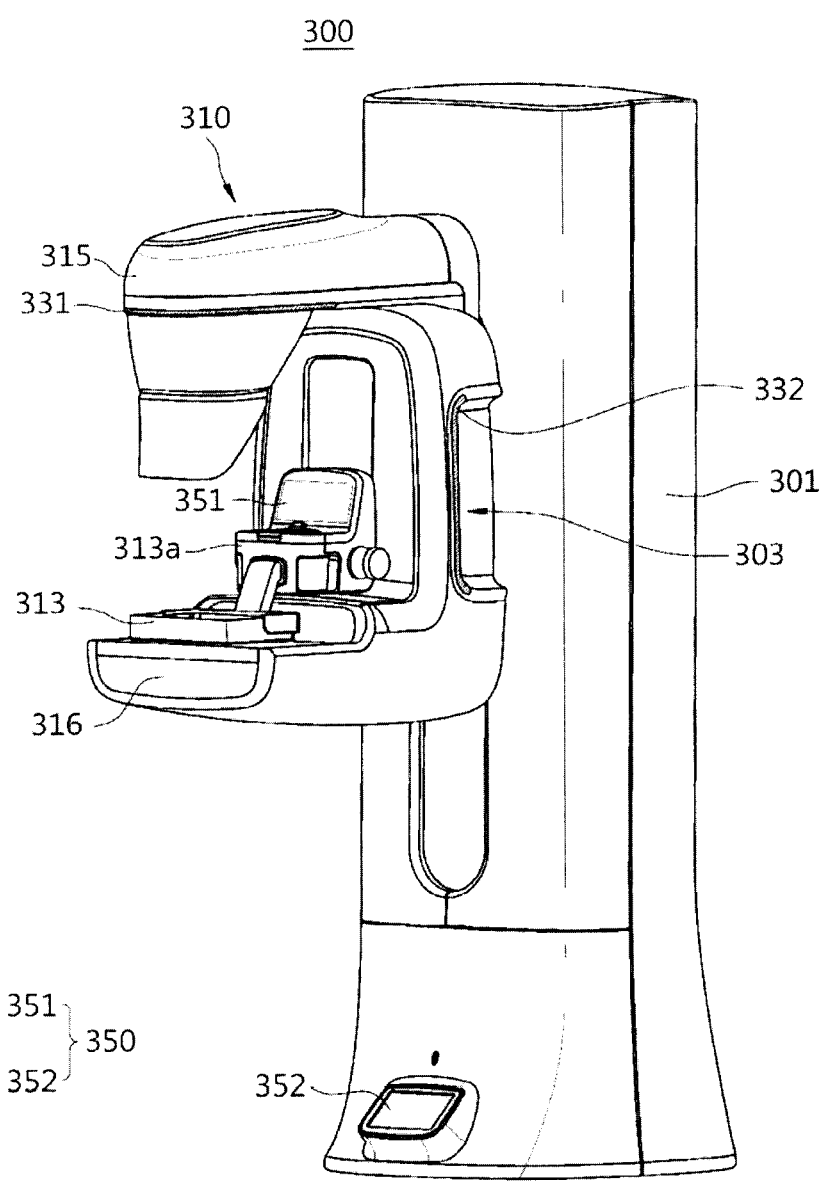
FIG. 10 illustrates the external appearance of the X-ray imaging apparatus shown in FIG. 9.

FIG. 9 is a functional block diagram illustrating an X-ray imaging apparatus, 300, according to another embodiment of the present disclosure. FIG. 10 illustrates an example external appearance of the X-ray imaging apparatus shown in FIG. 9.

Referring to FIG. 9, X-ray imaging apparatus 300 may include an X-ray tube 311, an X-ray detector 312, a controller 320, an illumination unit 330, an image processor 340, and a sub-display unit 350.

The X-ray tube 311, the X-ray detector 312, and the image processor 340 may be identical to those of the embodiment shown in FIG. 1, and as such a detailed description thereof will herein be omitted for convenience of description.

The illumination unit 330 may be identical to the illumination unit 110 shown in the embodiment of FIG. 1. The sub-display unit 350 may be identical to the sub-display unit 250 shown in the embodiment of FIG. 6. That is, as shown in FIG. 10, the X-ray imaging apparatus 300 may direct users including a patient and a radiologist. The X-ray imaging apparatus 300 may include the illumination unit 330 configured to provide ongoing procedure information of the X-ray imaging; and a sub-display unit 350 configured to display information regarding a scan process, information regarding the patient posture, information regarding the patient, information regarding the arm 210, or information regarding the acquired X-ray image.

In operation of the X-ray imaging apparatus 300, when scan information, visual interaction, or feedback information is supplied to the user, the illumination and the display are simultaneously used, such that the efficiency of the X-ray imaging apparatus 300 can be increased.

Meanwhile, although not shown in FIG. 10, the X-ray imaging apparatus 300 may include a workstation that includes not only a display unit configured to display either the captured X-ray image or a screen image associated with control of the X-ray imaging apparatus 200, but also an input unit configured to receive a control command regarding the X-ray imaging apparatus 300 from the user.

Figure 11:
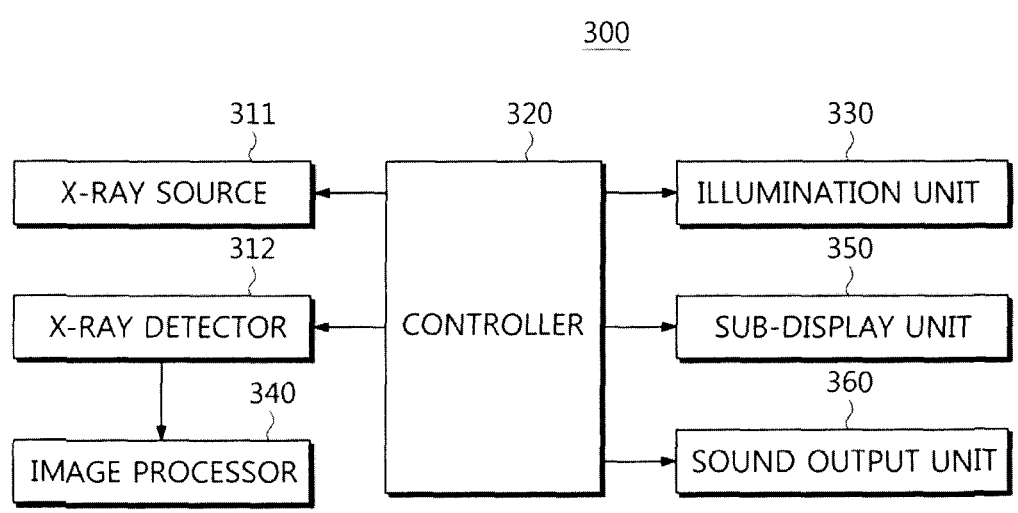
FIG. 11 is a functional block diagram illustrating an X-ray imaging apparatus further including a sound output unit.
Figure 12:
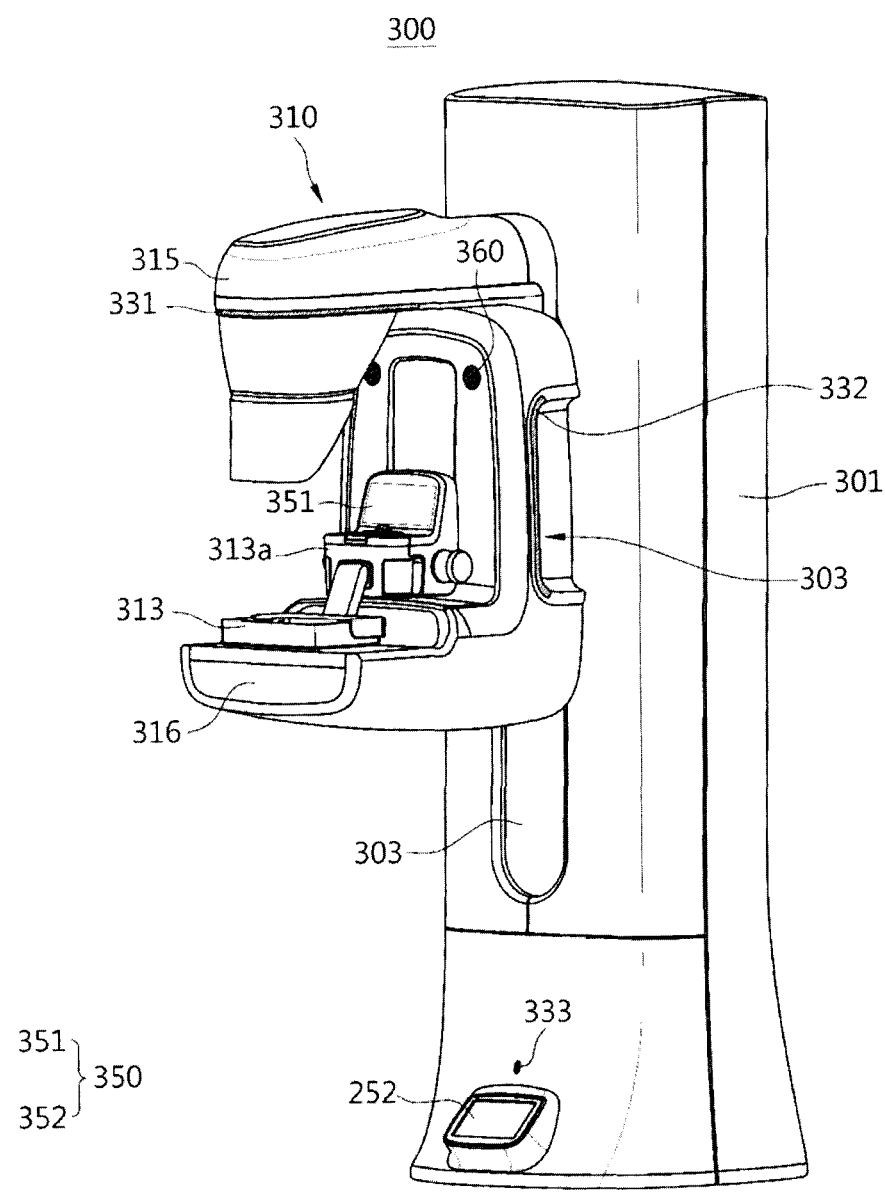
FIG. 12 illustrates the external appearance of the X-ray imaging apparatus shown in FIG. 11.

FIG. 11 is a functional block diagram illustrating an X-ray imaging apparatus 300 which further includes a sound output unit. FIG. 12 illustrates an example external appearance of the X-ray imaging apparatus shown in FIG. 11.

X-ray imaging apparatus 300 of FIG. 11 may include the illumination unit 330, the sub-display unit 350, and the sound output unit 360. The sound output unit 360 may audibly (and optionally, visually) provide the scanning information, the interaction information, or the feedback information to the user.

As shown in FIG. 12, the sound output unit 360 may be implemented as a speaker, and one or more sound output units 360 may be mounted at one or more locations of the arm 310. Alternatively, the sound output unit(s) 360 may not be directly mounted to the arm 310, or may also be mounted to the compression paddle 313 or the paddle mounting unit 313a. As still another option, the sound output unit 360 may be mounted to the gantry 310, and may also be mounted to both the arm 310 and the gantry 301. The sound output unit 360 may be arranged at any position at which the user can hear the sound during the X-ray imaging procedure; the precise position or size of the sound output unit 360 is not limited to the above examples.

In the embodiment of FIGS. 11 and 12, the interaction information, or the feedback information can be visually and audibly provided, and thus a workload of the radiologist can be further reduced. More information can thereby be more effectively provided to the user.

Detailed example procedures using the X-ray imaging apparatus 300 will hereinafter be described with reference to FIGS. 11 and 12.

Figure 13:
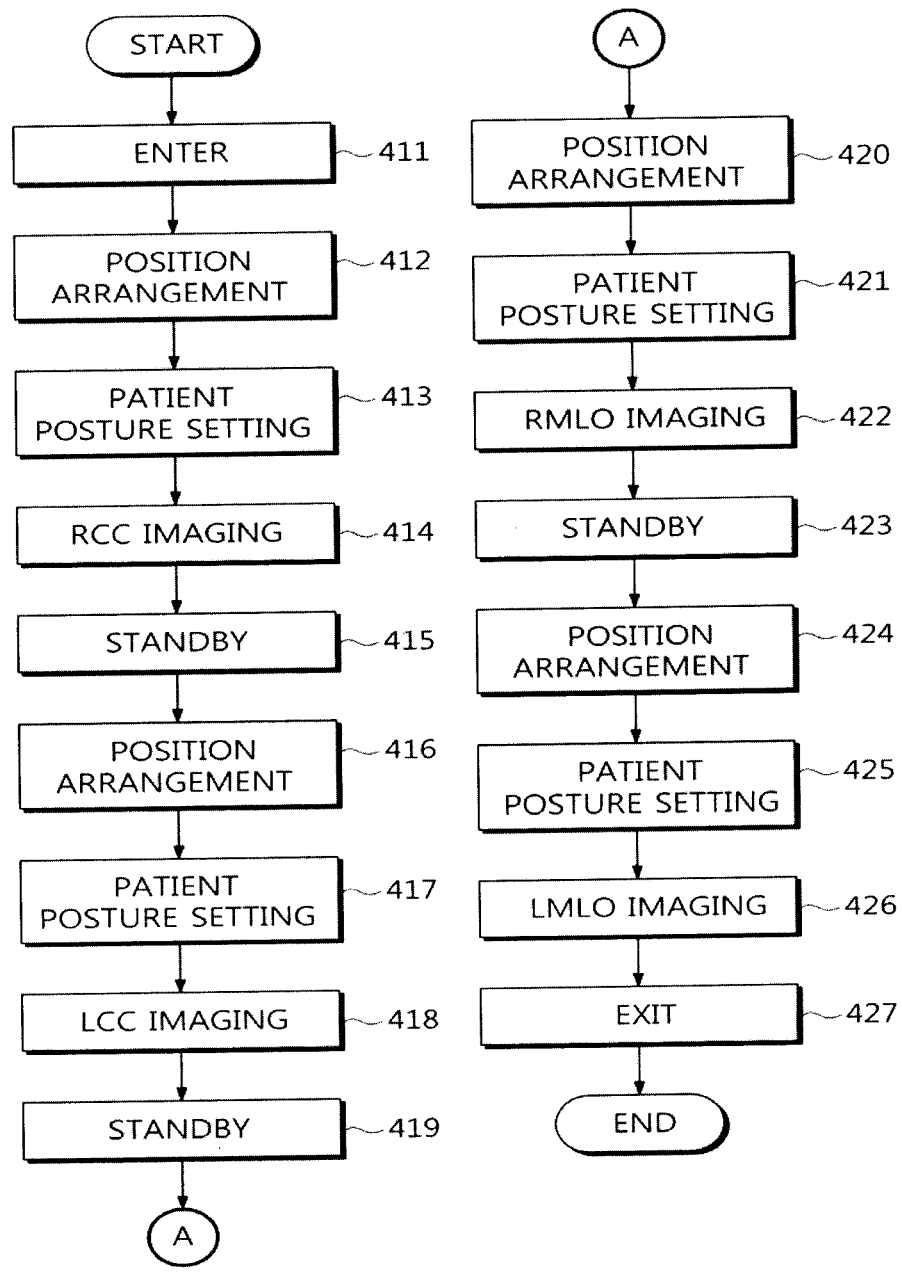
FIG. 13 is a flowchart illustrating the overall workflow applicable to the case in which an X-ray image of the breast is captured.

FIG. 13 is a flowchart illustrating an overall procedure applicable to the case in which an X-ray image of the breast is captured. FIGS. 14 to 28 illustrate either audiovisual information or feedback information supplied from the X-ray imaging apparatus 300 to a patient or radiologist in respective steps constituting a procedure.

Referring to FIG. 13, if the patient enters the room in which the X-ray imaging apparatus 300 is located in operation 411, the patient stands at the position at which the breast can be placed on the detector mounting unit 316.

If the patient stands at an appropriate position, the radiologist directs the patient posture, compresses the breast of the patient using the compression paddle 313, and performs image capture of the compressed breast. In this case, the patient posture may be established in different ways according to capturing categories. For example, the breast imaging may include mediolateral oblique projection (MLO) imaging and craniocaudal (CC) imaging. By way of example, it is assumed in the illustrative procedure of FIG. 13 that the right breast is both MLO-imaged (i.e., Right MLO (RMLO)) and CC-imaged ("RCC"), and the left breast is also MLO imaged ("LMLO") and CC-imaged ("LCC").

For RCC imaging indicating CC imaging of the right breast, the position of the arm 310 is arranged in operation 412. If the position of the arm 310 is arranged, the patient breast is located between the detector mounting unit 316 and the compression paddle 313, and is compressed. The arm and the head of the patient are located at positions suitable for imaging, such that the patient posture is established in operation 413. If the patient posture is fixed, RCC imaging is performed in operation 414, and the patient is in the standby mode before beginning the next image capturing in operation 415.

For LCC imaging indicating CC imaging of the left breast, the arm position is arranged in operation 416, the patient posture is established in operation 417, LCC imaging is performed in operation 418, and the patient is in the standby mode before beginning the next image capturing in operation 419.

For RMLO imaging indicating MLO imaging of the right breast, the arm position is arranged in operation 420, the patient posture is established in operation 421, RMLO imaging is performed in operation 422, and the patient is in the standby mode before beginning the next image capturing in operation 423.

For LMLO imaging indicating MLO imaging of the left breast, the arm position is arranged in operation 424, the patient posture is established in operation 425, and LMLO imaging is performed in operation 426. The patient exits the examination room in operation 427.

Figure 14:
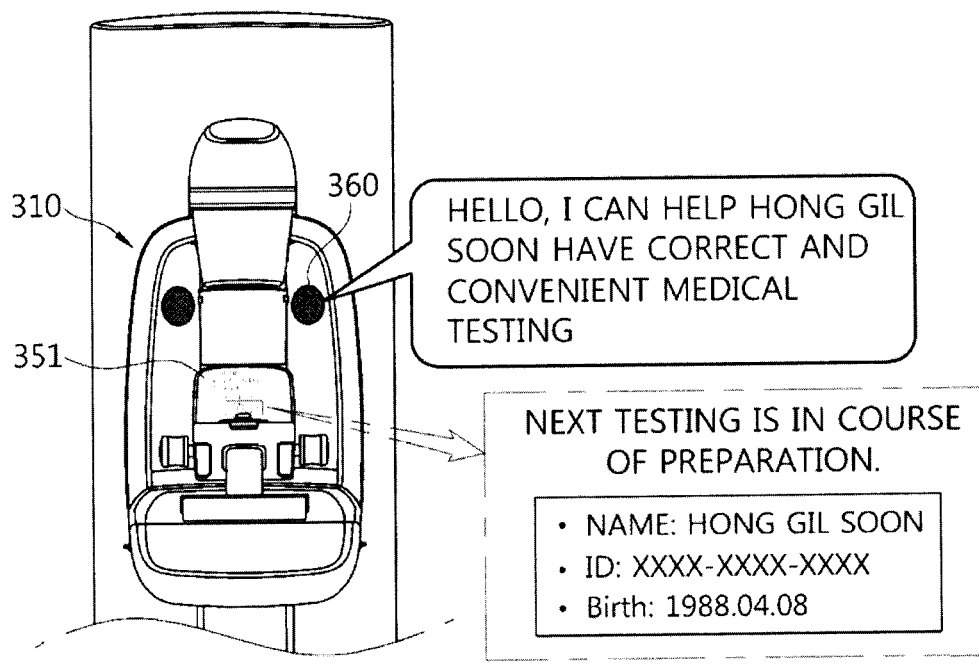
FIG. 14 illustrates audiovisual information provided when a patient enters an examination room.

Respective steps shown in FIG. 13 will hereinafter be described with reference to FIGS. 14 and 15, which illustrate audiovisual information provided when a patient enters an examination room.

In the X-ray imaging procedure, the captured image is stored using patient data (including a predetermined identifier (ID) of the patient, date of birth, etc.) as a tag, and the stored image may be used to diagnose or cure a disease of the patient. Therefore, it is desirable to recognize personal information of the patient prior to image capture. For this purpose, a screen image through which personal information shown in FIG. 14 can be confirmed, may be displayed as shown in FIG. 14, and an information guiding voice signal having patient data can be output through the sound output unit 360. The patient who enters the examination room compares either the patient data (name, ID, and the date of birth) displayed on the arm display unit 361 or the patient data (name) contained in the information guiding voice with personal information of the patient. If there is a difference between the patient data and the patient personal information, the radiologist is notified of such difference, such that the radiologist can prevent the wrong patient's image from being used for diagnosis or treatment of other patients.

If the patient personal information is identical to the patient data, the process for imaging starts. First, it is desirable for the patient to stand at a position at which the patient approaches close to the arm 310 in such a manner that the position of the arm 310 can be adjusted according to the breast position of the patient. For this purpose, as shown in FIG. 15, the gantry illumination unit 333 forms the line (L) at a specific position at which the patient preferably stands, the sound output unit 360 may output sound information for directing the patient position, and the same may be displayed as text content on the arm display unit 351.

After position arrangement of the arm 310 is completed, the patient can move close to the arm 310. Of course, provision of information shown in FIG. 15 may also be achieved after completion of the position arrangement of the arm 310.

Figure 16:
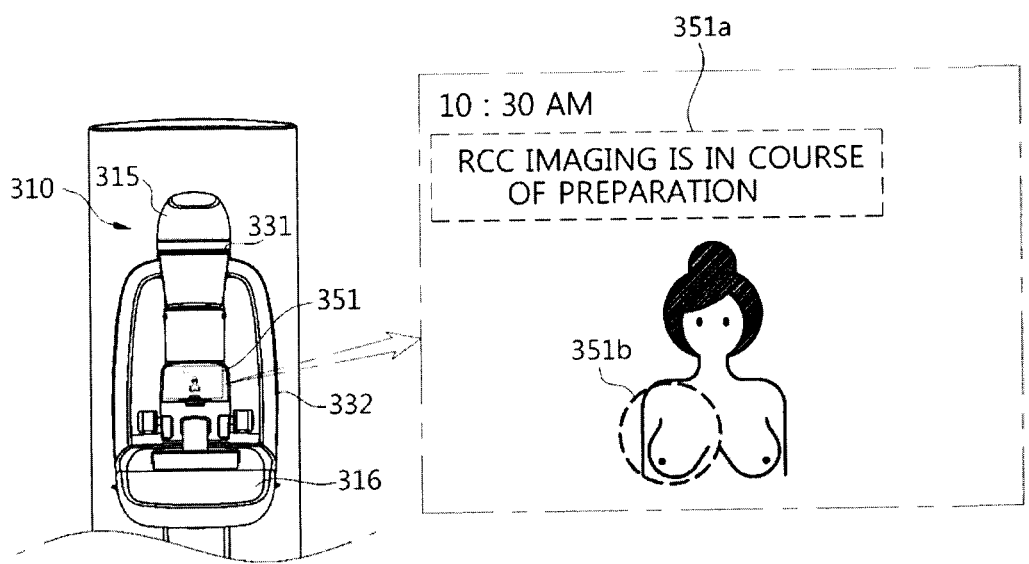
FIG. 16 illustrates information supplied to a user so as to capture a right craniocaudal (RCC) image.
Figure 17:
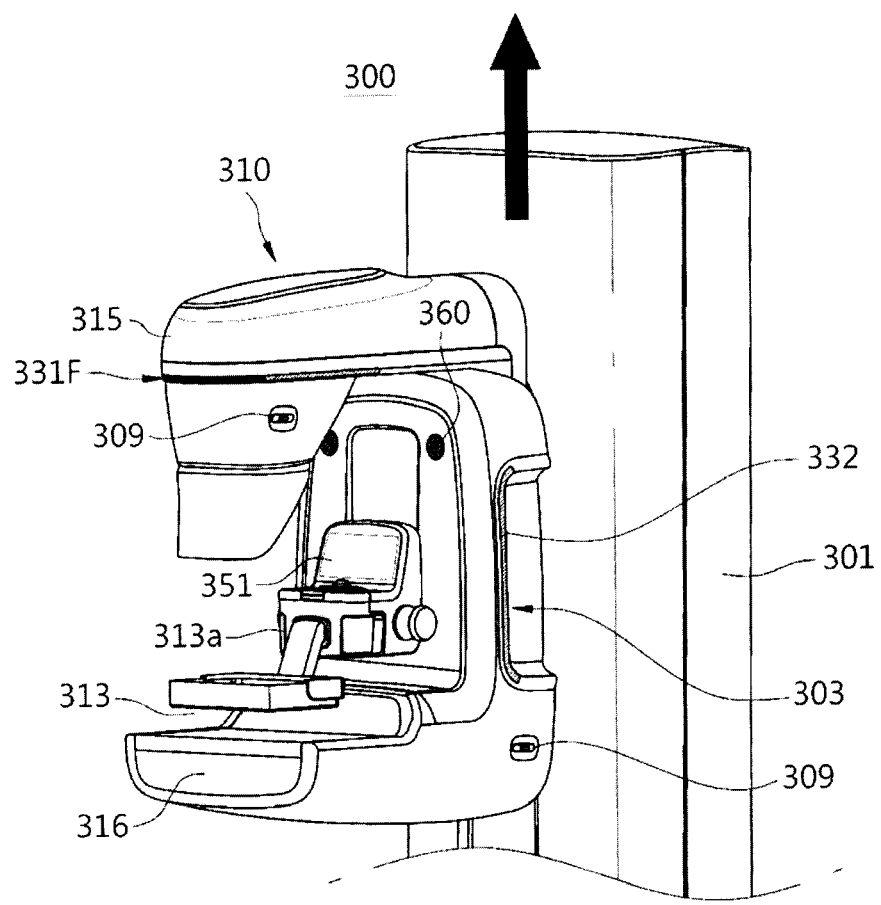
FIG. 17 is a perspective view of an example X-ray imaging apparatus 300 depicting vertical movement of the arm.

FIG. 16 illustrates information supplied to a user so as to capture a right craniocaudal (RCC) image. FIG. 16 illustrates not only the position of an arm arranged for RCC imaging but also a visual feedback supplied to a user. FIG. 17 is a perspective view of an example X-ray imaging apparatus 300 depicting vertical movement of the arm.

Information regarding the next image capturing to be performed in a subsequent process is supplied to the patient, and information regarding the next image capturing to be performed in a subsequent process can be supplied to the patient, whereby the patient may experience less anxiety. As shown in FIG. 16, information regarding the category of image capturing of a current step is displayed in the form of a text 351a and a picture 351b on the arm display unit 351. Thus the patient may have a better understanding of the image capturing procedural steps, and may prepare for the same. In addition, the radiologist can confirm the imaging progression step.

For the position arrangement of the arm 310, the user may directly apply external force needed for movement of the arm 310 in a desired direction to adjust the arm 310 to another position. The arm 310 may also be automatically adjusted via an electric motor. In this case, as shown in FIG. 17, the user may manipulate the input unit 309 mounted to at least one side of the arm 310 to cause automatic movement of the arm 310. In the illustrated example, the input unit 309 is shown as one control element mounted to an upper part and another element mounted to a lower part of the arm 310, thereby providing flexibility to the user. The input unit 309 may be implemented as a lever, a button, a jog-shuttle, or a combination thereof. The above are presented as merely examples. More or fewer control elements for the input unit 309 and various other positioning schemes and types of control elements are alternatively possible.

In order to automatically move the arm 310, a motor configured to generate power and drive devices (such as a gear) configured to transmit the generated power to the arm 310 may be embedded in the gantry 301. If the arm 310 is capable of moving automatically, the user is relieved from the burden of manually moving the heavy arm 310. CC imaging may be used to diagnose a subareolar and the breast. Therefore, when the position of the arm 310 is arranged for RCC imaging, a horizontal rotation angle of the arm 310 corresponds to 0 degrees with respect to the rotation shaft, and the vertical direction position of the arm 310 is adjusted to the breast position of the patient. From the front viewpoint of the arm 310, a shaft arranged in a vertical direction is referred to as a rotation shaft.

The user (patient or radiologist) may manipulate the input unit 309 so as to move the arm 310 in an upward direction, as depicted by the arrow in FIG. 17. For upward movement, a lever mounted to the center part of the input unit 309 may be moved upward.

If the user inputs a command needed for moving the arm 310 in the upward direction using the input unit 309, a front headlamp 331F of the headlamp 331 may blink as shown in FIG. 17, thereby supplying feedback information regarding the input command to the user. Alternatively, the color of the front headlamp 331F may be changed. The user may recognize the input command by viewing the change of the front headlamp 331F. If a command desired by the user is an upward movement command of the arm 310, this command can be confirmed via the feedback. In other embodiments, the system may be designed so that a series of input commands (e.g., a series of lever manipulations) are needed to automatically move the arm 310, thereby preventing accidental movement. Alternatively, if no additional command is input within a predetermined reference time, the command may be confirmed.

If the command is confirmed, the arm 310 moves upward. If the arm 310 reaches a desired position, the user may perform manipulation needed to stop the movement.

Meanwhile, during movement of the arm 310, information regarding quantitative information may be displayed on the sub-display units (351,352). If the arm 310 moves in the vertical direction to prepare for CC imaging as shown in the above example, the movement distance may be displayed in real time.

Figure 18:
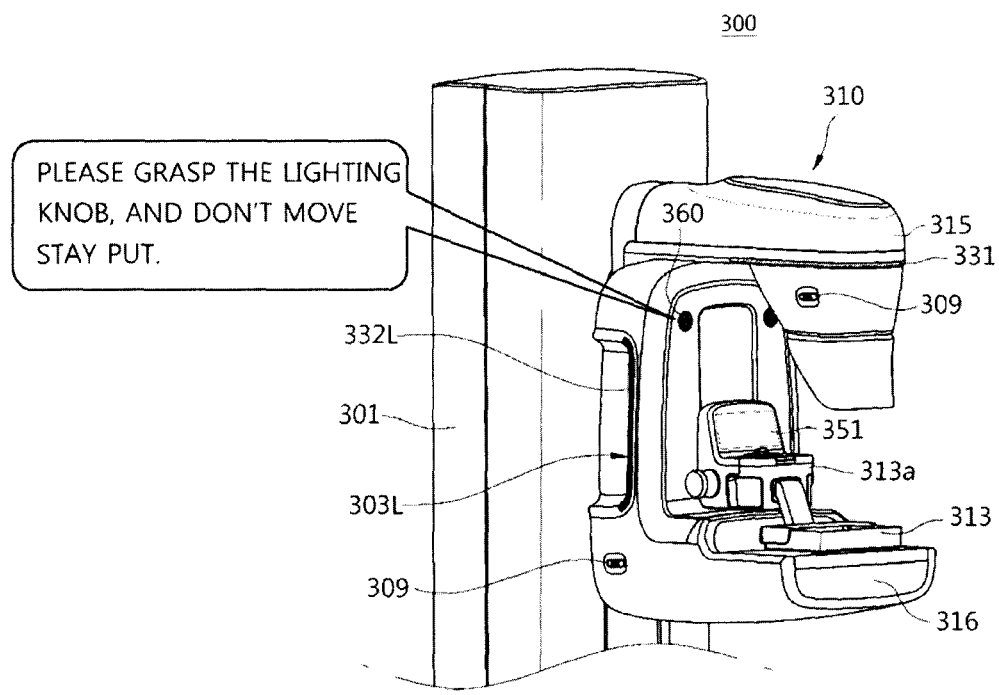
FIG. 18 illustrates audiovisual information supplied to a user when the patient posture is established for RCC imaging.

FIG. 18 illustrates audiovisual information supplied to a user when the patient posture is established for RCC imaging.

If the position of the arm 310 is sufficiently established for RCC imaging, the patient posture is established in operation 413. Under the condition that the patient breast is located between the compression paddle 313 and the detector mounting unit 316, the radiologist turns the patient's head in the opposite direction (i.e., to the left) of the examination direction, and the patient's breast approaches close to the end of the detector mounting unit 316.

As shown in FIG. 18, the handle lamp 332L mounted to the left handle 303L is turned on, blinks, or is illuminated in different colors so as to direct the patient to grasp the left handle 303L of the arm 310. Simultaneously, the sound output unit 360 can output a voice command for directing the patient to grasp the handle 303L as well as to maintain his or her posture.

If the patient posture is completely established, the radiologist lowers the compression paddle 313 to compress the breast 10. In this case, pressure applied to the breast 10 by the compression paddle 313 may be displayed on at least one of the arm display unit 351 and the gantry display unit 352. For example, if the radiologist lowers the compression paddle 313 by manipulating the foot pedal with his or her feet, the magnitude of pressure displayed on the gantry display unit 352 is confirmed and the descending position of the compression paddle 313 can be adjusted.

If the patient posture is completely established, the radiologist moves to the workstation and manipulates the input unit mounted to the workstation, such that irradiation and detection of X-rays for RCC imaging can be performed.

Figure 19:
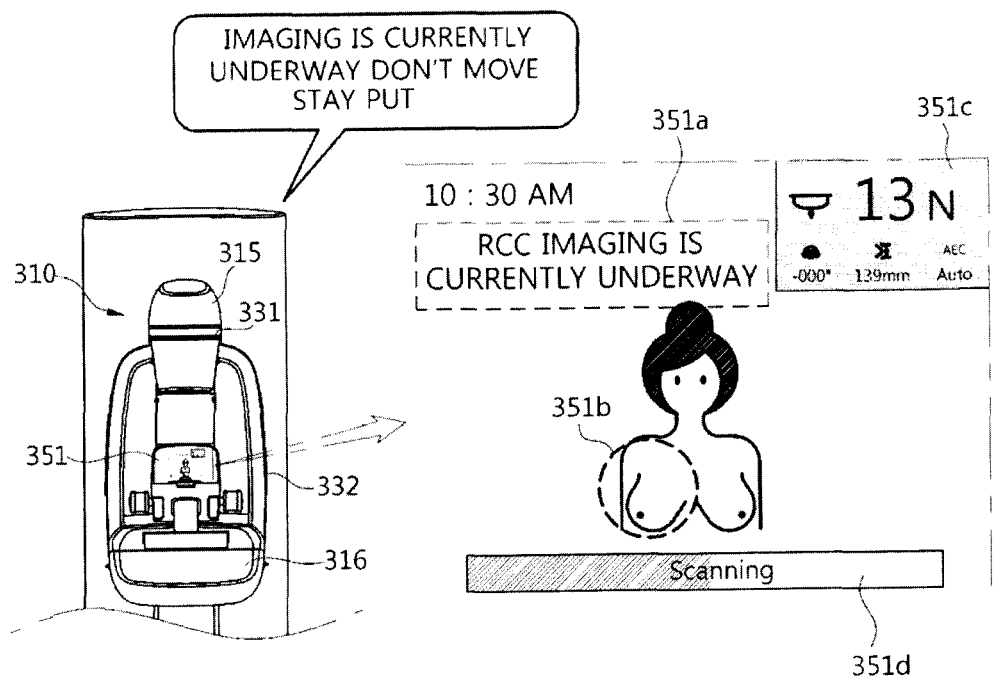
FIG. 19 illustrates visual information supplied to a user during RCC imaging.

FIG. 19 illustrates visual information that may be supplied to a user during RCC imaging. During RCC imaging, the arm display unit 351 may further display the window 351c including information regarding a state of the arm 310. For example, the window 351c may display a pressure of the compression paddle 313, a compression thickness, the rotation angle of the arm 310, etc. In addition, the bar 351d for indicating the ratio of the overall time of RCC imaging to the elapsed time may further be displayed in real time.

The sound output unit 360 may output a voice signal that informs the patient of the necessity of posture maintenance during image capture, and may inform the patient of information regarding the current progression situation. Information regarding the current progression situation may be recognized by the patient, such that patient posture maintenance can be directed repeatedly. If the patient posture is such that the patient has difficulty in viewing the arm display unit 351, necessary information can be obtained through the sound output unit 360.

Figure 20:
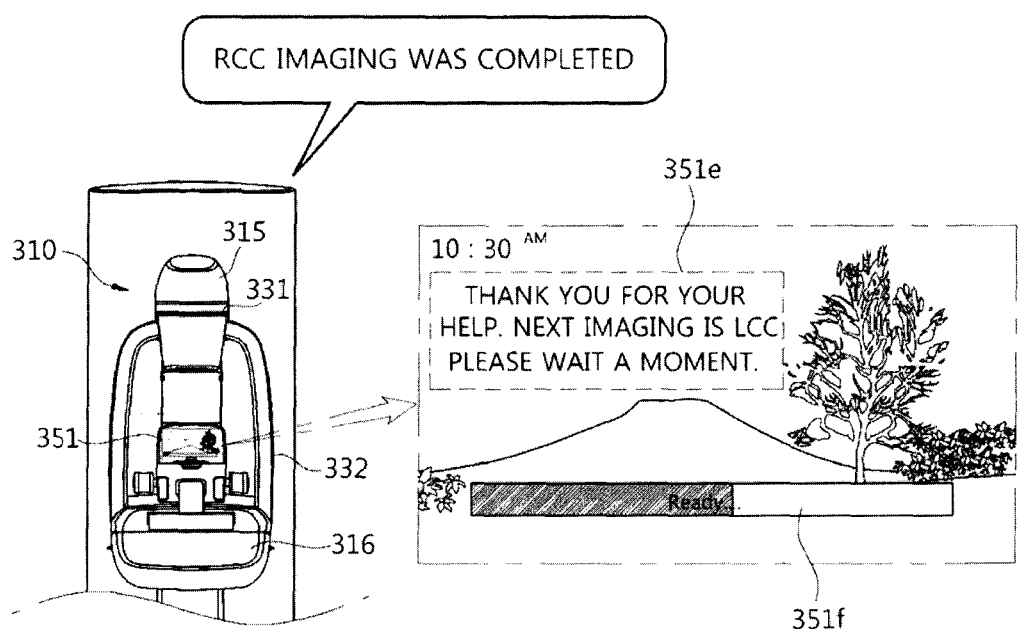
FIG. 20 illustrates visual and audio information supplied to a patient during a standby time for the next imaging.

FIG. 20 illustrates examples of visual and audio information supplied to a patient during a standby time for the next imaging. If RCC imaging is completed, the patient is in the standby mode for LCC imaging, which is the next image capturing in operation 415. If RCC imaging is completed, the sound output unit 360 may output sound information and may inform the patient of completion of image capture. If the radiologist acts to release compression, the arm display unit 351 may display a text 351e which provides information indicating that the next imaging is LCC imaging and requests a standby mode. In addition, the arm display unit 351 may further display the preparation state of the next image capturing, i.e., it may further display the bar 351f configured to visually display the residual time before the beginning the position arrangement of the arm 310.

Since LCC imaging is CC imaging performed on the left breast of the patient, the arm position arrangement 416, the patient posture setting 417, and the LCC imaging 418, excluding the situation in which the object to be captured is the left breast of the patient and some differences derived from this situation are similar to the above operations 412, 413 and 414. For convenience of description, only the aspects that differ will hereinafter be described in detail.

Figure 21:
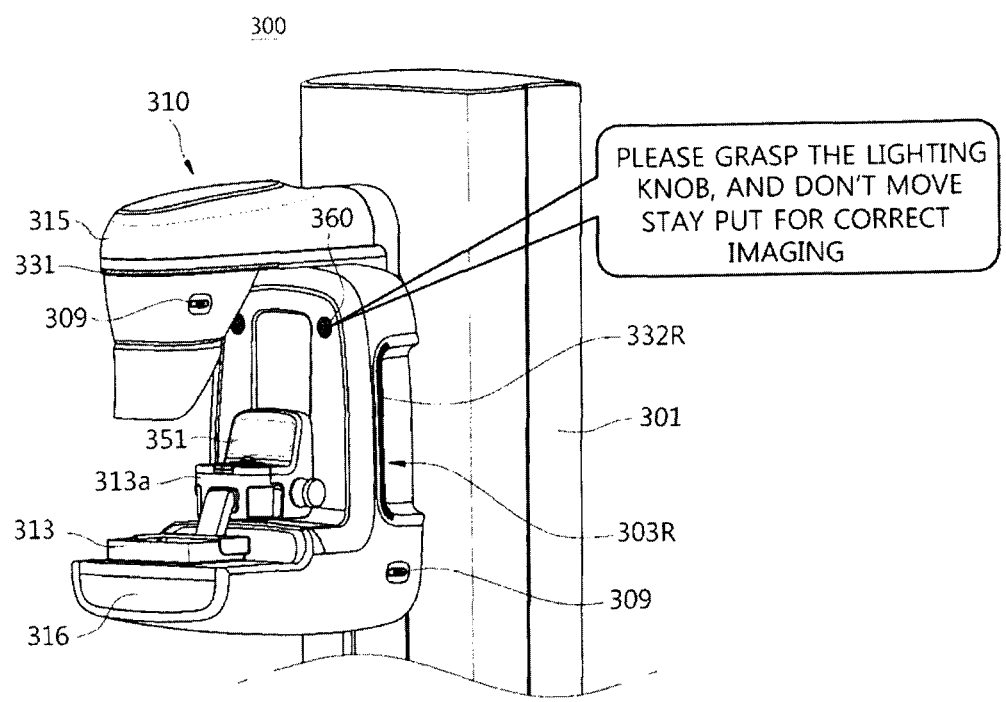
FIG. 21 illustrates visual and audio information supplied to a patient when the patient posture is established for left craniocaudal (LCC) imaging.

FIG. 21 illustrates visual and audio information supplied to a patient when the patient posture is established for LCC imaging. If the arm position for LCC imaging is arranged in operation 416, the radiologist may establish the patient posture in operation 417.

Under the condition that the patient breast is located between the compression paddle 313 and the detector mounting unit 316, the radiologist turns the patient's head in the opposite direction (i.e., to the right) of the examination direction, and the patient's breast approaches close to the end of the detector mounting unit 316.

As shown in FIG. 21, the handle lamp 332R mounted to the right handle 303R is turned on/off, blinks, or is illuminated in different colors so as to direct the patient to grasp the right handle 303R of the arm 310. Simultaneously, the sound output unit 360 can output a voice signal for directing the patient to maintain his or her posture.

If the patient posture is sufficiently established, the radiologist may compress the breast 10 by lowering the compression paddle 313.

MLO imaging is performed with the X-ray detector 312 located at the inferolateral side of the breast, where X-rays are emitted in a direction from the superomedial side to the inferolateral side of the breast. As shown in FIG. 13, the exemplary case in which MLO imaging (i.e., RMLO imaging) of the right breast and MLO imaging (i.e., LMLO imaging) of the left breast are performed will hereinafter be described in detail.

Figure 22:
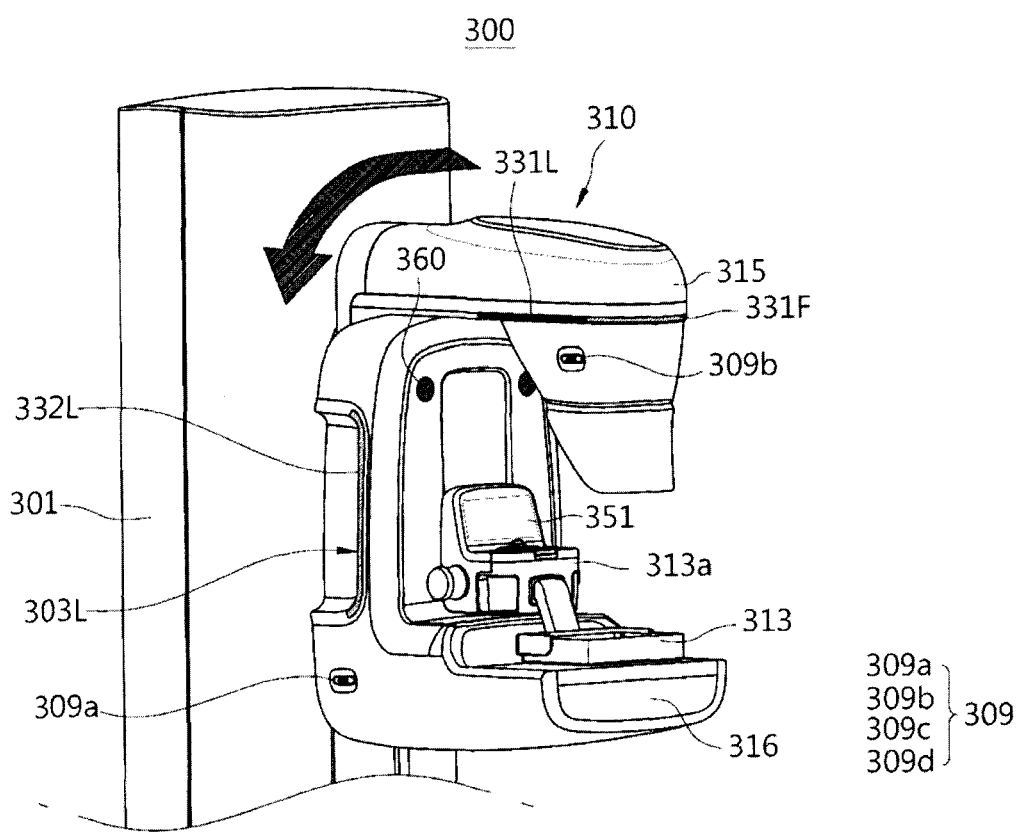
FIG. 22 illustrates a left side perspective view of an X-ray imaging apparatus and a rotational movement direction of an arm for RMLO imaging.
Figure 23:
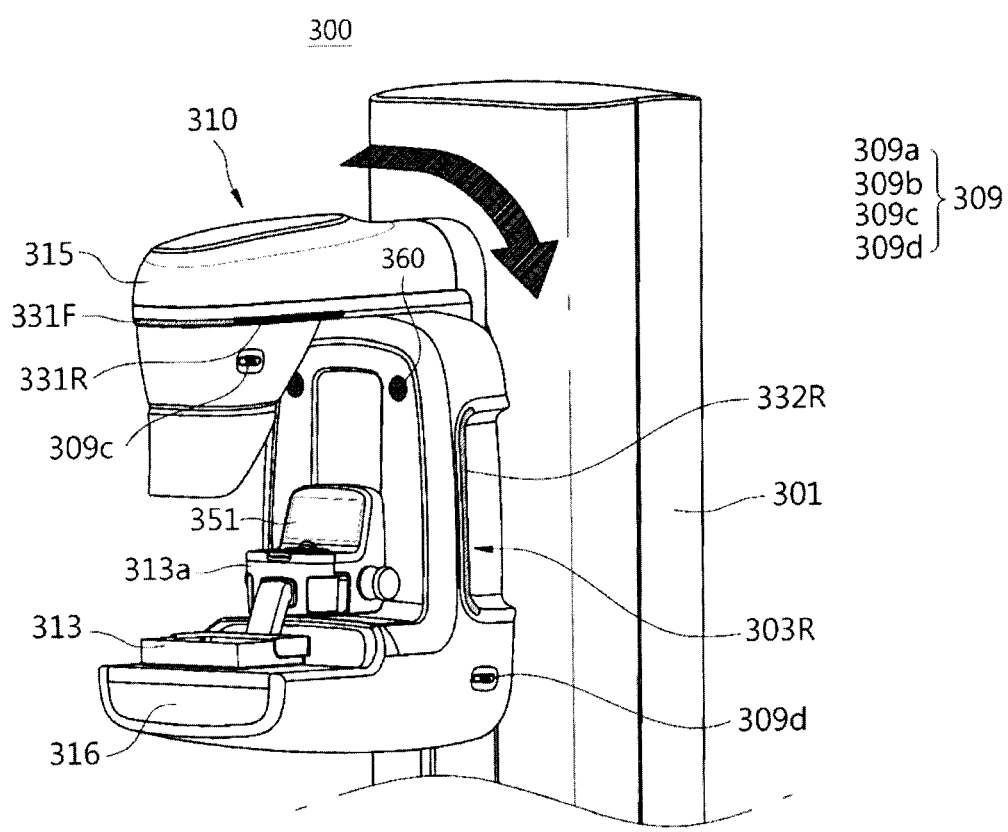
FIG. 23 illustrates a right side perspective view of an X-ray imaging apparatus and a rotational movement direction for LMLO imaging.

FIG. 22 illustrates a left side perspective view of imaging apparatus 300 and a rotational movement direction of an arm for RMLO imaging. FIG. 23 illustrates a right side perspective view of imaging apparatus 300 and a rotational movement direction for LMLO imaging. Visual feedback may be provided to the patient via display unit 351 in either case.

As described above, since the MLO imaging emits X-rays in the direction from the superomedial side to the inferolateral side of the breast, it is necessary for the RMLO imaging to turn the arm 310 to the left on the basis of the rotation shaft as shown in FIG. 22. The rotation angle can be selected from the range from 40° to 70° according to the patient physique. All directions used in the embodiments can be determined depending on the physical makeup of the patient. Therefore, the breast position of the patient is determined on the basis of the patient, and four directions (up, down, left, right) of the arm 310 may be determined on the basis of the patient undergoing imaging.

For RMLO imaging, the position of the arm 310 is arranged in operation 420. For this purpose, the radiologist may input a command for turning the arm 310 to the left by manipulating the input unit 309. In an example, the input unit 309 may include four control elements or buttons 309a, 309b, 309c and 309d. As shown in FIG. 22, the radiologist can press a left button 309a or 309b to input the corresponding command. If the radiologist inputs a command, as shown in FIG. 22, the left headlamp 331L of the headlamp 331 is turned on/off, blinks, or is illuminated in different colors, such that a feedback to the input command can be supplied to the radiologist. The radiologist can confirm his or her input command by viewing the left headlamp 331L. If a command desired by the radiologist indicates the left rotation of the arm 310, the command can be confirmed. For command confirmation, the corresponding manipulation may be repeated once more, and another manipulation allocated for such command confirmation may also be performed. Alternatively, if no additional command is input within a predetermined reference time, the command can also be confirmed.

If the command is confirmed, the arm 310 turns to the left and reaches a desired rotation angle. If the desired rotation angle is achieved, the radiologist may perform manipulation for movement stoppage.

If position arrangement of the arm 310 for RMLO imaging is completed, the patient posture is established in operation 421. The patient grasps the right handle 303R using the right arm. For this purpose, as shown in FIG. 21, the handle lamp 332R mounted to the right handle 303R is turned on/off, blinks or is illuminated in different colors, such that the handle lamp 332R may direct the patient to grasp the right handle 303R. Simultaneously, the sound output unit 360 outputs sound information such that it can direct the patient to perform grasping or posture maintenance.

If the patient posture is sufficiently established, the radiologist moves to the workstation and manipulates the input unit mounted to the workstation, such that irradiation and detection of X-rays for RMLO imaging 422 can be performed.

During the RMLO imaging, or during the standby time in which the patient waits for the next image capturing process after completion of RMLO imaging, visual information regarding the current progression situation can be supplied to the patient as shown in FIGS. 19 and 20.

For LMLO imaging, the position of the arm 310 is arranged in operation 420. For LMLO imaging, as shown in FIG. 23, the arm 310 may be rotated to the right on the basis of the rotation shaft as shown in FIG. 23. The rotation angle can be selected from the range from 40° to 70° according to patient physique.

For this purpose, the radiologist may input a command for turning the arm 310 to the right by manipulating the input unit 309. As shown in FIG. 23, the radiologist may press a right button 309c or 309d so as to input the corresponding command. If the radiologist inputs the command, as shown in FIG. 23, the right headlamp 331R of the headlamp 331 is turned on/off, blinks, or is illuminated in different colors, such that a feedback to the input command can be supplied to the radiologist. The radiologist can confirm his or her input command by viewing the right headlamp 331R. If a command desired by the radiologist indicates the right rotation of the arm 310, the command can be confirmed. For command confirmation, the corresponding manipulation may be repeated once more, and other manipulation allocated for such command confirmation may also be performed. Alternatively, if no additional command is input within a predetermined reference time, the command may also be confirmed.

If the command is confirmed, the arm 310 turns to the right and reaches a desired rotation angle. If the desired rotation angle is achieved, the radiologist may perform manipulation to stop the movement.

If position arrangement of the arm 310 for LMLO imaging is completed, the patient posture is established in operation 421. The patient grasps the left handle 303L using the left arm. For this purpose, as shown in FIG. 18, the handle lamp 332L mounted to the left handle 303L is turned on/off, blinks or is illuminated in different colors, such that the handle lamp 332L may direct the patient to grasp the left handle 303L. Simultaneously, the sound output unit 360 outputs sound information such that it can direct the patient to perform grasping and/or posture maintenance.

If the patient posture is sufficiently established, the radiologist moves to the workstation and manipulates the input unit mounted to the workstation, such that irradiation and detection of X-rays for LMLO imaging 426 can be performed.

During the LMLO imaging, visual information regarding the current progression situation can be supplied to the patient as shown in FIG. 19.

Figure 24:
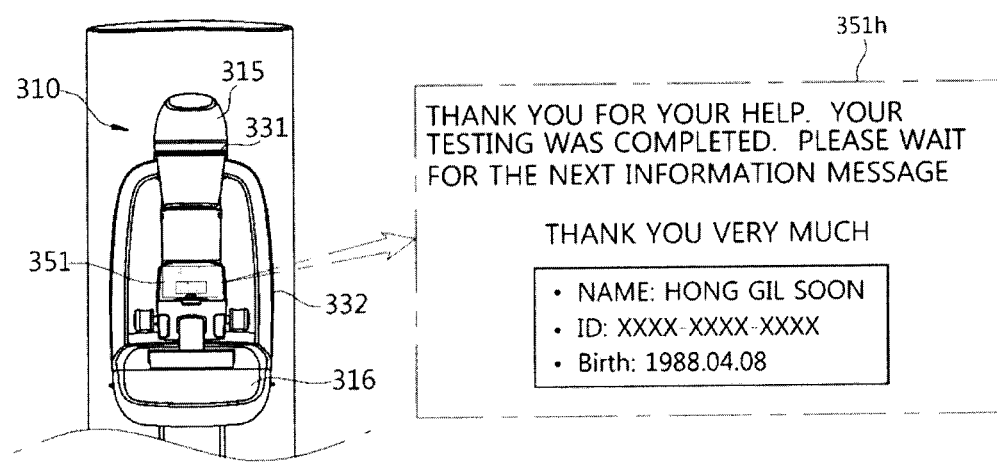
FIG. 24 illustrates visual and audio information supplied to a patient when all scanning processes are terminated.

FIG. 24 illustrates visual and audio information supplied to a patient when all X-ray imaging processes are terminated. If LMLO imaging is terminated, a screen image 351h including text data that indicates completion of all imaging processes and directs the patient to exit the examination room may be displayed on the arm display unit 351. In addition, sound information indicating the same content may also be output through the sound output unit 360.

Although the above-mentioned embodiments have exemplarily disclosed that the patient breast is RCC-, LCC-, RMLO-, and LMLO-imaged, the above-mentioned embodiments are merely examples applicable to the X-ray imaging apparatuses (100, 200, 300), the scope of the present technology is not limited thereto, and other imaging schemes can also be applied in other embodiments. Various other imaging schemes applicable to the patient breast may be performed, for example, 90° mediolateral imaging, 90° lateromedial imaging, 30° oblique imaging, Eklund compression imaging, etc. Audiovisual information or feedback information may be output through the sub-display unit 350, the illumination unit 330, and the sound output unit 360 according to the respective imaging schemes.

The sub-display unit 350, the illumination unit 330, and the sound output unit 360 may be controlled by the controller 320. For this purpose, the controller 320 may determine a current step from among the overall procedural sequence. Decision of the controller 320 may be based on user input, or may be based on the operations of other constituent elements. For example, if the user inputs a start command and a termination command of the X-ray imaging, the controller 320 may control at least one of the sub-display unit 350, the illumination unit 330, and the sound output unit 360 on the basis of the input command, such that entrance and exit of the patient can be directed.

Alternatively, under the condition that a predetermined sequence is completely performed, if LMLO imaging is completed as shown in FIG. 13, this means that X-ray imaging has been completed, such that patient exit can be guided.

In addition, in order to provide appropriate information when the patient posture is established and imaged in different ways according to imaging categories, the controller 320 may determine the imaging category in the current step on the basis of the position of the arm 310 arranged in the previous step, or may determine the imaging category in the current step on the basis of a predetermined sequence. In addition, if the position of the arm 320 is confirmed so that the arm 320 does not move any more, this may mean that the position arrangement of the arm 320 is completed and the patient posture setting is initiated. In addition, if X-rays are irradiated, this may signify the beginning of the imaging process, such that information indicating the imaging ongoing state may be provided. If irradiation of X-rays is stopped, this may mean the completion of one imaging process, such that information indicating the standby state of the next imaging or information indicating the patient exiting may be provided.

The above-mentioned examples are merely some examples from among various schemes for allowing the controller 320 to determine a current step, however, the scope or spirit of the X-ray imaging apparatus 300 according to the present technology is not limited thereto. A current step can be determined by various schemes other than the above-mentioned examples, and associated control may also be performed as necessary.

Meanwhile, the image acquired through the imaging may be displayed on the display unit mounted to the workstation. In addition, the acquired image may also be displayed on the sub-display unit 350, and a method for displaying the captured image on the sub-display unit 350 will hereinafter be described in detail.

Figure 25:
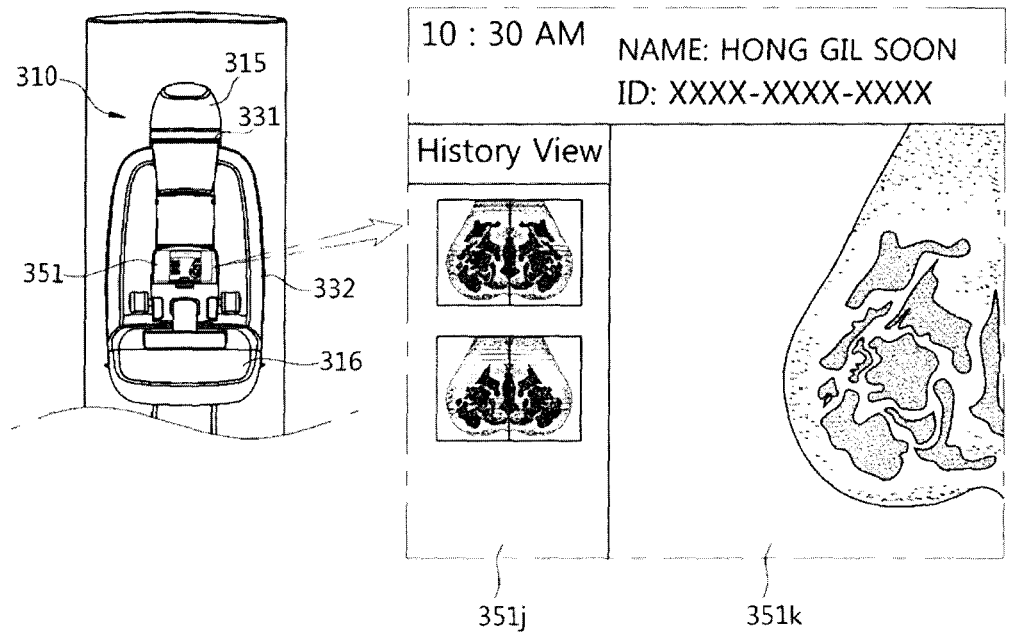
FIG. 25 illustrates an example of the captured mammogram displayed on an arm display unit.
Figure 26:
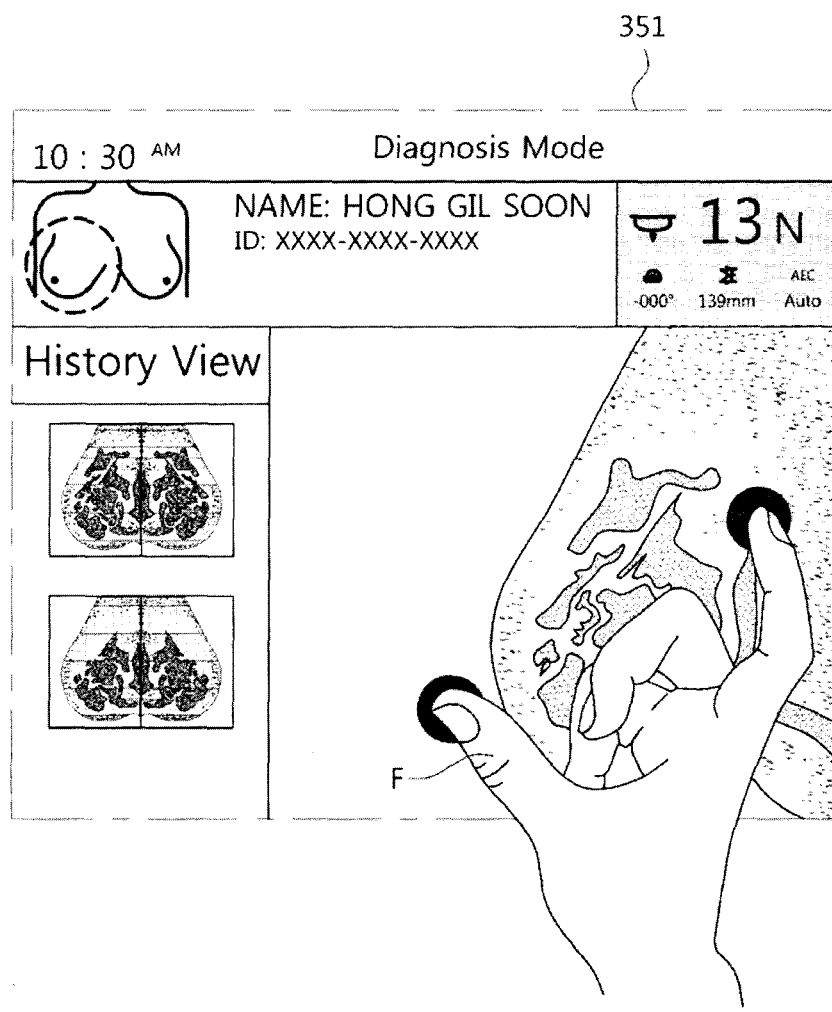
FIG. 26 depicts an exemplary method for allowing a user to manipulate the arm display unit.

FIG. 25 illustrates an example of the captured mammogram displayed on an arm display unit. FIG. 26 depicts an exemplary method for allowing a user to manipulate the arm display unit.

Referring to FIG. 25, the arm display unit 351 may display a currently captured mammogram 351k, and at the same time may display a previous mammogram 351j. The radiologist may compare the current mammogram with the previous mammogram, so that the radiologist can recognize a state of the patient, a lesion position, and whether re-imaging is necessary.

If the arm display unit 351 is implemented as a touch-screen, the user may input a desired command by touching the screen image of the arm display unit 351. For example, as shown in FIG. 26, the radiologist performs a pinch-in gesture, i.e., touches two points on the screen image using two fingers (F) and then reduces the spacing between two fingers (F) such that the screen image can be zoomed in (or out). In addition, if the radiologist increases the spacing between two fingers (F), the screen image can be zoomed out (or in). Alternatively, if the radiologist touches the screen image using two fingers (F) and then performs dragging in a vertical direction, image panning may be carried out. In addition, the radiologist may manipulate the image displayed on the screen using a variety of touch input methods.

Figure 27:
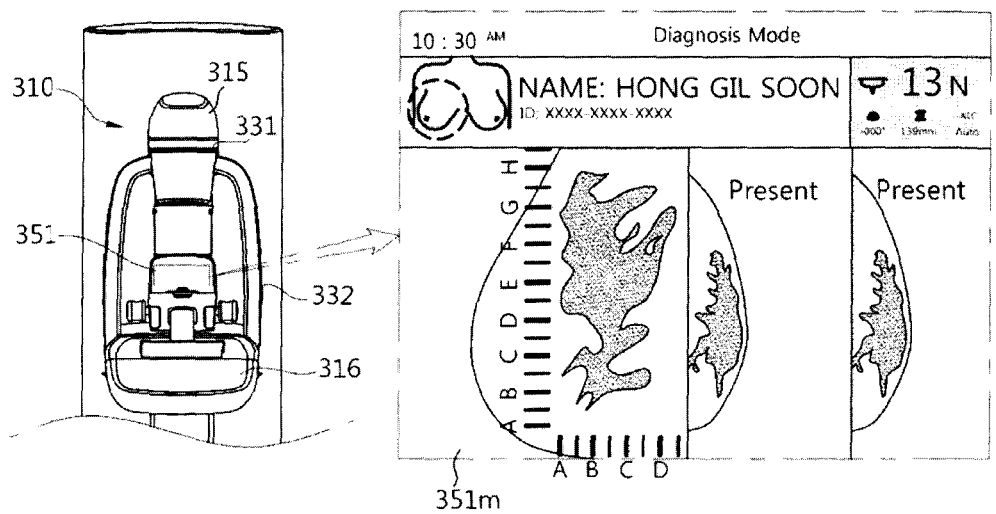
FIG. 27 depicts an exemplary method for confirming the position of a target through the captured image.
Figure 28:
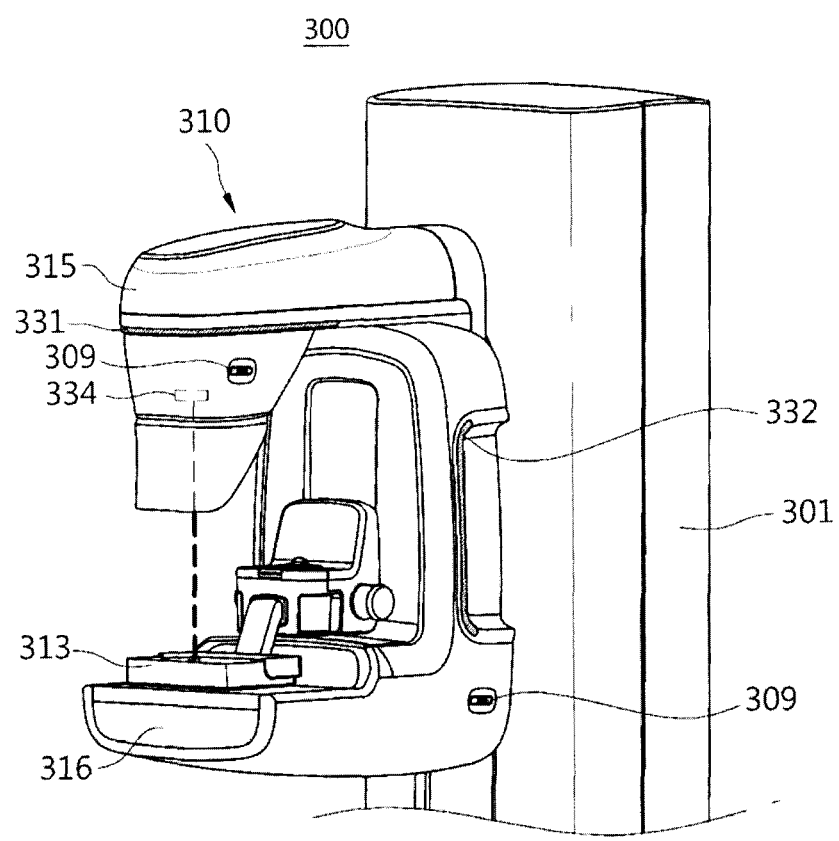
FIG. 28 depicts an exemplary method for guiding a biopsy after confirming the target position.

FIG. 27 depicts an exemplary method for confirming the position of a target through the captured image. FIG. 28 depicts an exemplary method for guiding a biopsy after confirming the target position.

If the captured image is used for biopsy, it is very important for the radiologist to correctly recognize the lesion position through the captured image. For this purpose, graduations indicating two-dimensional (2D) coordinates may be marked on the compression paddle 313, and the graduations may be displayed on the X-ray image in a form readable from the X-ray image. Image capturing is performed on the condition that the patient breast is compressed by the compression paddle 313 having graduations marked thereon, and the captured image 351m may be displayed on the arm display unit 351. Since the captured image 351m includes not only the patient mammogram but also the graduations displayed on the compression paddle 313, the user can confirm coordinates of the lesion by viewing the captured image 351m.

If the lesion coordinates are confirmed, a needle is inserted into the breast position corresponding to the lesion and localization is then performed. In order to insert the needle into the breast position (i.e., target position) corresponding to the lesion, the X-ray imaging apparatus 300 may further include a targeting light source 334 mounted to the tube head 315. The targeting light source 334 may emit light to the target position so that it can direct needle insertion. The targeting light source 334 can be implemented by various types of light sources, for example, a semiconductor laser, a He—Ne laser, a halogen lamp, an LED lamp, etc.

Moreover, a re-imaging process may be performed to recognize whether the needle is accurately inserted. The mammogram in which the needle is inserted may also be displayed on the arm display unit 351 after completion of the re-imaging process. The user may simultaneously recognize the image displayed on the arm display unit 351 and the position of a needle actually inserted into the breast, such that the user can decide whether to perform the re-imaging or treatment process.

Accordingly, as described above, an X-ray imaging apparatus in accordance with the present technology may include at least an X-ray tube, an X-ray detector, and an arm including an upper end within which the X-ray tube is disposed, and a lower end within which the X-ray detector is disposed. An illumination unit may be configured to provide an indication of a movement direction of the arm, responsive to a user input for moving the arm in the movement direction. A controller may control the illumination unit.

The illumination unit may change a lighting or blinking position thereof in response to the input movement direction of the arm.

The illumination unit may include a headlamp formed in the tube head.

The headlamp may include: a front headlamp formed at a front surface of the tube head; a left headlamp formed at a left side surface of the tube head; and a right headlamp formed at a right side surface of the tube head.

The controller may light or blink the front headlamp when the input movement direction of the arm is an upward direction.

The controller may light or blink the left headlamp when the input movement direction of the arm is a left direction.

The controller may light or blink the right lead lamp when the input movement direction of the arm is a right direction.

The controller, if the input movement direction of the arm is confirmed, may be configured to move the arm in response to the input movement direction.

The controller, if re-inputting of the arm movement direction does not occur after completion of one inputting of the arm movement direction, may be configured to determine that the input movement direction of the arm has been confirmed.

The controller, if a confirmation command of the input movement direction of the arm is input, may be configured to move the arm in response to the input movement direction.

The illumination unit may further include: a handle lamp formed in a handle mounted to the arm.

The controller may light or blink the handle lamp in a stage in which maintenance of a patient posture is needed for X-ray imaging.

The controller, if the arm movement is completed, may be configured to light or blink the handle lamp.

The illumination unit may further include a gantry lamp formed in a gantry configured to support the arm; and the controller may light the gantry lamp in an initial stage of a workflow needed for X-ray imaging, and thus guides a patient position.

The gantry lamp may be lighted on, and may thus form a line at a bottom part thereof.

The controller may control at least one color of the headlamp and the handle lamp in different ways according to a workflow stage needed for X-ray imaging.

The X-ray imaging apparatus may further include: a sub-display unit mounted to at least one of the arm and a gantry supporting the arm.

The sub-display unit may be detachably mounted to the arm or a gantry.

The sub-display unit may be configured to display information regarding a workflow needed for X-ray imaging.

The sub-display unit may be configured to display a captured X-ray image.

The sub-display unit may be configured to display at least one of a movement direction of the arm, a movement distance of the arm, a rotation angle of the arm, and pressure of a compression paddle.

As also described above, in accordance with another aspect of the present technology, an X-ray imaging apparatus includes: a tube head to which an X-ray tube is mounted; a detector mounting unit to which an X-ray detector is mounted; an arm including an upper end to which the tube head is mounted, and a lower end to which the detector mounting unit is mounted; a sub-display unit detachably mounted to at least one of the arm and a gantry supporting the arm; and a controller configured to control the sub-display unit.

The sub-display unit may include a mobile display device.

The sub-display unit may be configured to display a currently-captured X-ray image and at least one previously-captured X-ray image.

The sub-display unit may be configured to display information regarding a workflow needed for X-ray imaging.

The sub-display unit may be configured to display information regarding a current stage from among a plurality of stages constructing the workflow.

The sub-display unit may be configured to display at least one of a movement direction of the arm, a movement distance of the arm, a rotation angle of the arm, and pressure of a compression paddle.

The sub-display unit may be configured to display an X-ray image of a target object and graduations; and the controller may be configured to determine a position of a specific region contained in the target object on the basis of the displayed graduations.

As is apparent from the above description, the X-ray imaging apparatus according to embodiments described herein can guide the patient posture using a visual or audible interaction device during execution of mammography, and can provide the patient with information about the ongoing procedure during the mammography execution, such that it can allow the patient to feel comfortable, can reduce workload of a radiologist or a physician, and can improve the accuracy of X-ray imaging.

The above-described methods according to the present disclosure can be implemented in hardware, firmware or with the use of software or computer code that can be stored in a recording medium such as a CD ROM, an RAM, a floppy disk, a hard disk, or a magneto-optical disk or computer code downloaded over a network originally stored on a remote recording medium or a non-transitory machine readable medium and to be stored on a local recording medium, so that the methods described herein can be rendered using such software that is stored on the recording medium using a general purpose computer, or a special processor or in programmable or dedicated hardware, such as an ASIC or FPGA. As would be understood in the art, the computer, the processor, microprocessor controller or the programmable hardware include memory components, e.g., RAM, ROM, Flash, etc. that may store or receive software or computer code that when accessed and executed by the computer, processor or hardware implement the processing methods described herein. In addition, it would be recognized that when a general purpose computer accesses code for implementing the processing shown herein, the execution of the code transforms the general purpose computer into a special purpose computer for executing the processing shown herein. No claim element herein is to be construed under the provisions of 35 U.S.C. 112, sixth paragraph, unless the element is expressly recited using the phrase "means for."

Although several particular embodiments of the present disclosure have been shown and described, it would be appreciated by those skilled in the art that changes may be made in these embodiments without departing from the principles and spirit of the invention, the scope of which is defined in the claims and their equivalents.

What is claimed is:
1. An X-ray imaging apparatus comprising:
an X-ray tube;
an X-ray detector;
an arm including an upper end within which the X-ray tube is disposed, and a lower end within which the X-ray detector is disposed;
an input configured to receive user input for moving the arm in a movement direction;
an illumination unit located on the arm, configured to signal a movement direction of the arm, after a user input for moving the arm in the movement direction from the input, wherein the illumination unit is separate from the input; and a controller configured to control the illumination unit.

2. The X-ray imaging apparatus according to claim 1, wherein the illumination unit changes a lighting state or blinking position thereof in response to the movement direction of the arm.

3. The X-ray imaging apparatus according to claim 1, wherein the illumination unit includes a headlamp formed in the upper end of the arm, and wherein the headlamp includes:
- a front headlamp formed at a front surface of the arm;
- a left headlamp formed at a left side surface of the arm; and
- a right headlamp formed at a right side surface of the arm.

4. The X-ray imaging apparatus according to claim 3, wherein the front headlamp blinks after receiving a user input from the input that is separate from the illumination unit to move the arm in an upward direction.

5. The X-ray imaging apparatus according to claim 3, wherein the left headlamp turns on or blinks after receiving the user input that is separate from the illumination unit from the input to move the arm in a left direction.

6. The X-ray imaging apparatus according to claim 3, wherein the right headlamp turns on or blinks after receiving the user input from the input that is separate from the illumination unit to move the arm a right direction.

7. The X-ray imaging apparatus according to claim 3, wherein the controller commands the arm to move in response to an input command confirming the movement direction.

8. An X-ray imaging apparatus comprising:
an X-ray tube;
an X-ray detector;
an arm including an upper end within which the X-ray tube is disposed, and a lower end within which the X-ray detector is disposed;
an input configured to receive user input for moving the arm in a movement direction;
an illumination unit located on the arm, configured to signal a movement direction of the arm, after a user input for moving the arm in the movement direction from the input, wherein the illumination unit is separate from the input; and
a controller configured to control the illumination unit, wherein the illumination unit includes:
a headlamp formed in the upper end of the arm; and:
a handle lamp formed in a handle mounted to the arm.

9. The X-ray imaging apparatus according to claim 8, wherein the controller lights or blinks the handle lamp in a stage in which maintenance of a patient posture is needed for X-ray imaging.

10. The X-ray imaging apparatus according to claim 8, wherein if the arm movement is completed, the controller causes the handle lamp to be illuminated steadily or to blink.

11. The X-ray imaging apparatus according to claim 1, wherein:
the illumination unit includes a headlamp formed in the upper end of the arm, and a gantry lamp formed in a gantry configured to support the arm; and
the controller lights the gantry lamp in an initial stage of a procedure used for X-ray imaging, sufficient to guide a patient position.

12. The X-ray imaging apparatus according to claim 8, wherein the controller controls at least one color of the headlamp and the handle lamp in different ways according to a procedural stage in X-ray imaging.

13. The X-ray imaging apparatus of claim 1, wherein the illumination unit illuminates a line on the ground, said line on the ground indicating a position for a patient to stand.

* * * * *